(12) United States Patent
Hagiwara et al.

(10) Patent No.: US 8,435,717 B2
(45) Date of Patent: *May 7, 2013

(54) COMPOUND FOR PHOTOACID GENERATOR, RESIST COMPOSITION USING THE SAME, AND PATTERN-FORMING METHOD

(75) Inventors: Yuji Hagiwara, Kawagoe (JP); Jonathan Joachim Jodry, Kawagoe (JP); Satoru Narizuka, Saitama (JP); Kazuhiko Maeda, Hino (JP)

(73) Assignee: Central Glass Company, Limited, Ube-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/527,362

(22) PCT Filed: Feb. 14, 2008

(86) PCT No.: PCT/JP2008/052410
§ 371 (c)(1),
(2), (4) Date: Oct. 14, 2009

(87) PCT Pub. No.: WO2008/099869
PCT Pub. Date: Aug. 21, 2008

(65) Prior Publication Data
US 2010/0035185 A1    Feb. 11, 2010

(30) Foreign Application Priority Data

Feb. 15, 2007 (JP) ................. 2007-034834
Mar. 15, 2007 (JP) ................. 2007-066236
May 30, 2007 (JP) ................. 2007-143879
May 30, 2007 (JP) ................. 2007-143880

(51) Int. Cl.
*G03F 7/004* (2006.01)
*G03F 7/039* (2006.01)
*G03F 7/038* (2006.01)
*G03C 1/675* (2006.01)
*G03C 1/73* (2006.01)

(52) U.S. Cl.
USPC ........ 430/270.1; 430/919; 430/920; 430/921; 430/924; 430/925; 430/907; 430/910; 548/542; 548/545; 548/548; 546/243; 546/346; 544/158; 544/173; 560/117; 560/129; 558/47; 558/48; 558/51; 558/52; 558/54; 562/100; 562/103; 562/113; 568/30; 568/35

(58) Field of Classification Search .................. None
See application file for complete search history.

(56) References Cited

U.S. PATENT DOCUMENTS

| | | | |
|---|---|---|---|
| 6,749,987 B2 | 6/2004 | Kodama et al. | |
| 6,893,792 B2 | 5/2005 | Miya et al. | |
| 7,435,526 B2 | 10/2008 | Kodama et al. | |
| 2002/0102491 A1* | 8/2002 | Kodama et al. | 430/270.1 |
| 2005/0147920 A1* | 7/2005 | Lin et al. | 430/311 |
| 2006/0228648 A1 | 10/2006 | Ohsawa et al. | |
| 2007/0003871 A1 | 1/2007 | Kodama et al. | |
| 2007/0264596 A1 | 11/2007 | Ohsawa et al. | |
| 2009/0148791 A1 | 6/2009 | Kodama et al. | |
| 2009/0234155 A1 | 9/2009 | Oh et al. | |
| 2009/0291390 A1 | 11/2009 | Jung et al. | |
| 2010/0075256 A1 | 3/2010 | Joo et al. | |
| 2010/0304303 A1 | 12/2010 | Maeda et al. | |
| 2011/0015431 A1 | 1/2011 | Jodry et al. | |
| 2011/0034721 A1 | 2/2011 | Hagiwara et al. | |

FOREIGN PATENT DOCUMENTS

| | | |
|---|---|---|
| EP | 1 710 230 A1 | 10/2006 |
| JP | 2002-214774 A | 7/2002 |
| JP | 2004-4561 A | 1/2004 |
| JP | 2004-117959 A | 4/2004 |
| JP | 2007-304490 A | 11/2007 |
| KR | 10-2006-0107340 A | 10/2006 |

OTHER PUBLICATIONS

"Perfluorooctyl Sulfonates; Proposed Significant New Use Rule", Federal Register Environmental Documents, Environmental Protection Agency, Oct. 18, 2000, vol. 65, No. 202 (Thirty-five (35) pages).
International Search Report with partial English translation dated Apr. 15, 2008 (Seven(7) pages).
Korean Office Action dated Jul. 25, 2011 (Eleven(11) pages).
Japanese-language translation of Korean Office Action dated Nov. 2, 2012 (nine (9) pages) (submitted on Jan. 15, 2012).
Korean Office Action dated Nov. 2, 2012 (seven (7) pages).

* cited by examiner

*Primary Examiner* — Sin J. Lee
(74) *Attorney, Agent, or Firm* — Crowell & Moring LLP

(57) ABSTRACT

A sulfonic acid onium salt represented by the following formula (1) can be used as a superior radiosensitive acid generator for resist compositions. It is possible to form a good pattern by using a resist composition containing this sulfonic acid onium salt.

[Chemical Formula 64]

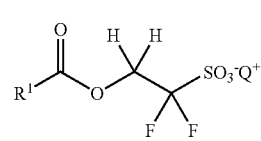

(1)

In formula (1), $R^1$ represents a monovalent organic group, and $Q^+$ represents a sulfonium cation or iodonium cation.

17 Claims, No Drawings

COMPOUND FOR PHOTOACID GENERATOR, RESIST COMPOSITION USING THE SAME, AND PATTERN-FORMING METHOD

TECHNICAL FIELD

The present invention relates to photoacid generator, which is useful as a chemically amplified resist material suitable for a micro-processing technology, particularly photolithography, in the production steps of semiconductor devices and the like, and to a fluorine-containing sulfonate (for example, a fluorine-containing, sulfonic acid onium salt) or fluorine-containing, sulfonic acid group-containing compound (for example, a fluorine-containing sulfonic acid), which constitutes the same. Furthermore, the present invention relates to a resist composition, which is characterized in containing the photoacid generator, and to a pattern-forming method using this resist composition.

BACKGROUND OF THE INVENTION

In recent years, the trend toward micro-scale pattern rule has been increasing with the trend toward large-scale integration and high-speed of LSI. The trend toward a shorter wavelength of the exposure light source lies behind it. For example, it has become possible to mass-produce DRAM (dynamic random-access memory) of 64M-bit (processing dimension is 0.25 µm or less) by the wavelength shortening from mercury lamp i-line (365 nm) to KrF excimer laser (248 nm). Furthermore, in order to realize the production of DRAM's having integration degrees of 256M and 1G or greater, a lithography using ArF excimer laser (193 nm) has been studied on a full scale, and a 65 nm node device has been studied by a combination with a high NA lens (NA≧0.9). Although the use of $F_2$ laser having a wavelength of 157 nm had been named as a candidate for the production of the next 45 nm node devices, the application was postponed by many problems represented by cost increase of scanner, change of optical system, low etching resistance of resist, and the like. As an alternative to $F_2$ lithography, proposed was ArF immersion lithography. Now, the development is going on toward its early introduction.

As a resist suitable for such exposure wavelength, "chemically amplified resist material" attracts much attention. This contains a radiosensitive acid generator (hereinafter referred to as "photoacid generator"), which generates an acid by radiation irradiation (hereinafter, referred to as "exposure"), and is a pattern-forming material that forms a pattern by making a difference in solubility between the exposed portion and the unexposed portion through a reaction using the acid generated by the exposure as a catalyst.

As the photoacid generator used for such chemically amplified resist material, onium sulfonates, such as iodonium sulfonate and sulfonium sulfonate, sulfonic acid esters, N-imidosulfonate, N-oximesulfonate, o-nitrobenzylsulfonate, trismethanesulfonate of pyrogallol, and the like are known.

The acids generated from these photoacid generators upon exposure are alkanesulfonic acids, arylsulfonic acids, and partially or entirely fluorinated arylsulfonic acids, alkanesulfonic acids, and the like.

Of these, acid generators that generate partially or entirely fluorinated alkanesulfonic acids have a sufficient acid strength against deprotection reactions of protective groups that are difficult in deprotection, and therefore many of them have been put into practical use. As the examples, it is possible to mention triphenylsulfonium trifluoromethanesulfonate, triphenylsulfonium perfluoro-n-octanesulfonate, and the like.

However, in the case of triphenylsulfonium trifluoromethanesulfonate, the acid to be generated becomes a sufficiently strong acid, and the resolution performance as a photoresist becomes sufficiently high, but it has a defect of high mask dependency as a photoresist due to low boiling point of the acid and due to long diffusion length of the acid. Furthermore, in the case of triphenylsulfonium perfluoro-n-octanesulfonate, it has a sufficient acidity and is almost appropriate in terms of acid boiling point and diffusion length. Therefore, it attracts much attention in recent years. However, in the case of considering environmental problems, radiosensitive acid generators having such perfluoroalkylsulfonyl structure are generally low in combustibility, and human body accumulation is also suspected. Thus, there is a proposal of limiting the use in a report (Non-patent Publication 1) by the US ENVIRONMENTAL PROTECTION AGENCY.

Under such background, there have been the developments of acid generators that generate partially or entirely fluorinated alkanesulfonic acids and that have characteristics of having a sufficient acidity, of being appropriate in terms of acid boiling point and diffusion length, and of having less burden on the environment. Thus, there have been the developments of alkoxycarbonylfluoroalkanesulfonic acid onium salts as acid generators, such as triphenylsulfonium methoxycarbonyldifluoromethanesulfonate (Patent Publication 1), (4-methylphenyl)diphenylsulfonyl t-butoxycarbonyldifluoromethane sulfonate (Patent Publication 2), or triphenylsulfonium (adamantan-1-ylmethyl)oxycarbonyldifluoromethanesulfonate (Patent Publication 3).

Patent Publication 1: Japanese Patent Application Publication No. 2004-117959
Patent Publication 2: Japanese Patent Application Publication No. 2002-214774
Patent Publication 3: Japanese Patent Application Publication No. 2004-4561
Non-patent Publication 1: Perfluorooctyl Sulfonates; Proposed Significant New Use Rule [Oct. 18, 2000 (Volume 65, Number 202)]

Then, there have been reported resist compositions containing these acid generators and pattern-forming methods using such resist compositions.

SUMMARY OF THE INVENTION

Since the above-mentioned alkoxycarbonylfluoroalkanesulfonic acid onium salts are produced from high-price raw materials, the acid generators themselves are also high-priced.

On the other hand, in the case of conducting a finer line width control, it has become important that chemically amplified resist is not only superior in resolution performance, but also superior in flatness of the film surface after the resist pattern formation. A chemically amplified resist that is inferior in flatness of the film surface lowers in pattern dimension precision, as a result of transfer of roughness condition (nano edge roughness) of the film surface to substrate when resist pattern is transferred to substrate by a treatment such as etching. Therefore, it is known that at last electric characteristics of a device tend to be damaged.

Furthermore, in order to obtain a superior flatness too, a photoacid generator used for such chemically amplified resist materials is required to be homogeneously dispersed in a resist composition. Therefore, solubility of photoacid generator in resist solvent and compatibility with resin are extremely important.

From such viewpoint, it is a task of the present invention to provide a fluorine-containing sulfonate or fluorine-containing sulfonic acid group-containing compound that shows good flammability and has no problem in human body accumulation, that not only acidity of acid (photogenerated acid) to be generated is sufficiently high, and acid (photogenerated acid) to be generated has an appropriate boiling point, but also diffusion length in resist film becomes appropriately short, and that is furthermore superior in solubility in resist solvent and compatibility with resin, and that is low-priced, as a radiosensitive acid generator that responds to active radiations, particularly KrF excimer laser, ArF excimer laser, or far ultraviolet radiation represented by EUV, electron beam, etc., and to provide a photoacid generator containing the same.

It is another task of the present invention to provide a resist composition containing the photoacid generator and to provide a pattern-forming method that good pattern shape is obtained by using such resist composition.

The present inventors have repeated an eager study to solve the above tasks. As a result, we have reached to finding a fluorine-containing sulfonate or fluorine-containing sulfonic acid group-containing compound, having a structure represented by formula (A)

[Chemical Formula 1]

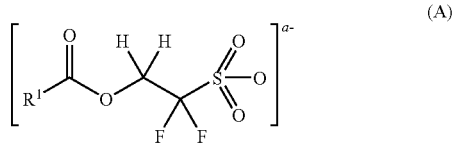

(A)

(in the formula, $R^1$ represents a $C_{1-10}$ straight-chain or branched alkyl group (herein hydrogen atoms of the alkyl group may partially or entirely be replaced with fluorine or hydroxyl group, and two hydrogen atoms on the same carbon constituting the alkyl group may be replaced with a single oxygen atom to make a keto group), a $C_{1-10}$ straight-chain or branched alkenyl group having a double bond at an end portion at least (herein hydrogen atoms of the end alkenyl group may partially or entirely be replaced with fluorine or hydroxyl group, and two hydrogen atoms on the same carbon constituting the end alkenyl group may be replaced with a single oxygen atom to make a keto group), a $C_{3-20}$ alicyclic organic group (herein hydrogen atoms of the alicyclic organic group may partially or entirely be replaced with fluorine or hydroxyl group, and two hydrogen atoms on the same carbon constituting the alicyclic organic group may be replaced with a single oxygen atom to make a keto group), a $C_{6-20}$ aryl group, a $C_{1-10}$ straight-chain or branched alkoxyl group (herein hydrogen atoms of the alkoxyl group may partially or entirely be replaced with fluorine or hydroxyl group), a $C_{6-20}$ aryloxy group (herein hydrogen atoms of the aryloxy group may partially or entirely be replaced with fluorine or hydroxyl group), a $C_{2-10}$ straight-chain or branched alkylcarbonyl group (herein hydrogen atoms of the alkylcarbonyl group may partially or entirely be replaced with fluorine or hydroxyl group), a $C_{7-20}$ arylcarbonyl group (herein hydrogen atoms of the arylcarbonyl group may partially or entirely be replaced with fluorine or hydroxyl group), a $C_{2-10}$ straight-chain or branched alkylcarbonyloxy group (herein hydrogen atoms of the alkylcarbonyloxy group may partially or entirely be replaced with fluorine or hydroxyl group), a $C_{7-20}$ arylcarbonyloxy group (herein hydrogen atoms of the arylcarbonyloxy group may partially or entirely be replaced with fluorine or hydroxyl group), a $C_{1-10}$ straight-chain or branched alkoxycarbonyl group (herein hydrogen atoms of the alkoxycarbonyl group may partially or entirely be replaced with fluorine or hydroxyl group), or a $C_{7-20}$ aryloxycarbonyl group (herein hydrogen atoms of the aryloxycarbonyl group may partially or entirely be replaced with fluorine or hydroxyl group). a is 1 or 0.)

In the formula, in the case of a=1, the entirety in the angle bracket of formula (A) takes a negative monovalent anion. By a combination with a counter cation, the entirety of the chemical species becomes a fluorine-containing sulfonate. On the other hand, in the case of a=0, oxygen of "—O" at the right end in formula (A) is attached to another atom by a single bond, and the entirety of the chemical species becomes a fluorine-containing sulfonic acid group-containing compound.

Specifically, we have found novel fluorine-containing sulfonic acid onium salt, fluorine-containing N-sulfonyloxyimide compound and fluorine-containing oximesulfonate compound, and a novel photoacid generator containing any one of these three compounds, and have solved the above task by constituting a resist composition using the photoacid generator. Furthermore, we have found that a good pattern can be formed by using this resist composition, thereby completing the invention.

A photoacid generator contained in the resist composition of the present invention is assured of a sufficient flammability and is also assured of being low in human body accumulation, since the number of fluorine atoms in the main chain of the fluorine-containing sulfonate or fluorine-containing sulfonic acid group-containing compound (specifically, the fluorine-containing sulfonic acid onium salt, fluorine-containing N-sulfonyloxyimide compound or fluorine-containing oximesulfonate compound), which constitutes the same, is appropriately suppressed.

Furthermore, it is known that, with respect to acidity of acid (photogenerated acid) that is generated by light irradiation, the number of fluorine atoms at α-position of the sulfo group contributes greatly, but the number of fluorine atoms at β-position and beyond almost does not contribute. Therefore, fluorine atoms at β-position and beyond do not contribute to acidity, lower flammability, and lead to the increase of human body accumulation. On this point, a fluorine-containing sulfonic acid onium salt of the present invention has two fluorine atoms at α-position having a great contribution to acidity, thereby achieving high acidity by the minimum number of fluorine atoms.

Furthermore, the photoacid generator has a substituted carbonyloxy group at an end. Therefore, according to need, it is possible to introduce a substituent having a different structure and to freely control boiling point. Specifically, it is possible to make boiling point appropriately high by introducing a high molecular weight substituent or a bulky substituent.

Furthermore, a fluorine-containing sulfonic acid onium salt of the present invention has a structure of alkyl-substituted carbonyloxyfluoroalkanesulfonic acid. Fluorine-containing sulfonic acid onium salt, which has been proposed hitherto, is an alkoxycarbonylfluoroalkanesulfonic acid (for example, Japanese Patent Application Publication 2004-4561). As compared with this alkoxycarbonylfluoroalkanesulfonic acid, it has an opposite orientation of ester. Therefore, it is more stable in structure and is high in solubility in resist solvents and compatibility with resins. Furthermore, similar to boiling point, it is also possible to suitably adjust solubility and compatibility by changing substituent of the substituted carbonyloxy group, in accordance with resist solvent and resin to be used.

Furthermore, an acid generator of the present invention can be synthesized by using bromodifluoroethanol, which is a low-price raw material, as the raw material. Therefore, it is possible to provide an acid generator with a lower price.

Furthermore, according to the present invention, there is provided a fluorine-containing sulfonic acid onium salt represented by the following formula (1).

[Chemical Formula 2]

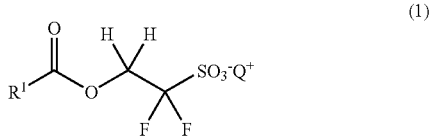

(1)

In the above formula (1), $R^1$ has the same meaning as that of $R^1$ in formula (A). $Q^+$ represents a sulfonium cation represented by the following formula (2), or an iodonium cation represented by the following formula (3).

[Chemical Formula 3]

(2)

In the above formula (2), $R^2$, $R^3$ and $R^4$ mutually independently represent $C_{1-30}$ straight-chain or branched alkyl groups optionally having substituents, $C_{3-30}$ cyclic monovalent hydrocarbon groups optionally having substituents, $C_{6-30}$ aryl groups optionally having substituents, or unsubstituted, monovalent, heterocyclic organic group of which number of atoms is 4-30. Any two or more of the above $R^2$, $R^3$ and $R^4$ may be connected to form a ring through sulfur atom.

[Chemical Formula 4]

(3)

In the above formula (3), $R^5$ and $R^6$ mutually independently represent $C_{1-30}$ straight-chain or branched alkyl groups optionally having substituents, $C_{3-30}$ cyclic monovalent hydrocarbon groups optionally having substituents, $C_{6-30}$ aryl groups optionally having substituents, or unsubstituted, monovalent, heterocyclic organic group of which number of atoms is 4-30. The above $R^5$ and $R^6$ may be connected to form a ring through iodine atom.

Furthermore, according to the present invention, there is provided a fluorine-containing sulfonic acid represented by the following formula (4).

[Chemical Formula 5]

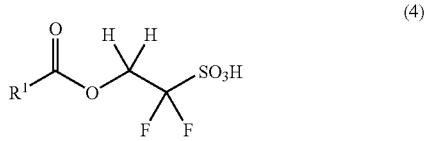

(4)

(In the above formula (4), $R^1$ has the same meaning as that of $R^1$ in formula (A).)

Furthermore, according to the present invention, there is provided a fluorine-containing sulfonate represented by the following formula (5).

[Chemical Formula 6]

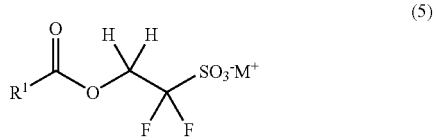

(5)

(In the above formula (5), $R^1$ has the same meaning as that of $R^1$ in formula (A). $M^+$ shows a monovalent cation.)

Furthermore, according to the present invention, there is provided a fluorine-containing N-sulfonyloxyimide compound represented by the following formula (6).

[Chemical Formula 7]

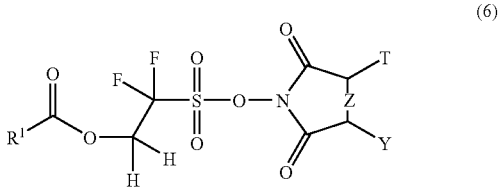

(6)

(In the above formula (6), $R^1$ has the same meaning as that of $R^1$ in formula (A). Z shows a single bond, double bond, methylene group or oxygen atom. T and Y independently show hydrogen atoms or $C_{1-10}$ substituted or unsubstituted alkyl groups, or T and Y jointly may form an alicyclic structure, aromatic ring structure or hetero ring structure by including carbon atoms to which they are attached.)

Furthermore, according to the present invention, there is provided a fluorine-containing oximesulfonate compound represented by the following formula (7).

[Chemical Formula 8]

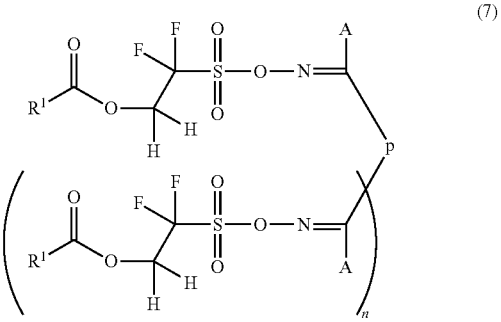

(7)

(In the above formula (7), $R^1$ has the same meaning as that of $R^1$ in formula (A). n represents 0 or 1. In case that n is 0, p represents a substituted or unsubstituted $C_{1-20}$ alkyl group, or substituted or unsubstituted $C_{6-15}$ aryl group. In case that n is 1, p represents a single bond, substituted or unsubstituted $C_{1-20}$ alkylene group, or substituted or unsubstituted $C_{6-15}$ arylene group. A represents a cyano group, trifluoromethyl group, perfluoroethyl group, perfluoropropyl group, 5H-perfluoropentyl group, 6H-perfluorohexyl group, nitro group or methyl group. In case that n is 1, both of A may be attached to each other, thereby forming a $C_6$ ring together with carbon atoms to which they are attached.)

Furthermore, according to the present invention, there is provided a photoacid generator containing the above-mentioned fluorine-containing sulfonic acid onium salt, fluorine-containing N-sulfonyloxyimide compound or fluorine-containing oximesulfonate compound.

Furthermore, according to the present invention, there is provided a method for producing the above-mentioned fluorine-containing sulfonic acid by irradiating the above-mentioned photoacid generator with light.

The above-mentioned fluorine-containing sulfonic acid onium salt is, for example, triphenylsulfonium 2-(1'-adamantane)carbonyloxy-1,1-difluoroethanesulfonate.

Furthermore, according to the present invention, in a resist composition containing a base resin, an acid generator and a solvent, there is provided a first resist composition characterized in that the acid generator is an acid generator that generates fluorine-containing sulfonic acid represented by the above formula (4).

Furthermore, according to the present invention, the first resist composition may be a second resist composition characterized in that the acid generator that generates fluorine-containing sulfonic acid represented by the above formula (4) is fluorine-containing sulfonic acid onium salt represented by the above formula (1).

Furthermore, according to the present invention, the first resist composition may be a third resist composition characterized in that the acid generator that generates fluorine-containing sulfonic acid represented by the above formula (4) is fluorine-containing N-sulfonyloxyimide compound represented by the above formula (6).

Furthermore, according to the present invention, the first resist composition may be a fourth resist composition characterized in that the acid generator that generates fluorine-containing sulfonic acid represented by the above formula (4) is fluorine-containing oximesulfonate compound represented by the above formula (7).

Furthermore, according to the present invention, any of the first to fourth resist compositions may be a fifth resist composition characterized in that the base resin is a polymer prepared by polymerizing at least one monomer selected from the group consisting of olefins, fluorine-containing olefins, acrylates, methacrylates, fluorine-containing acrylates, fluorine-containing methacrylates, norbornene compounds, fluorine-containing norbornene compounds, styrene-series compounds, fluorine-containing styrene-series compounds, vinyl ethers and fluorine-containing vinyl ethers, or copolymer prepared by copolymerizing at least two of the above monomers.

Furthermore, according to the present invention, any of the first to fourth resist compositions may be a sixth resist composition characterized in that the base resin is a polymer compound containing a repeating unit represented by the following formula (10).

[Chemical Formula 9]

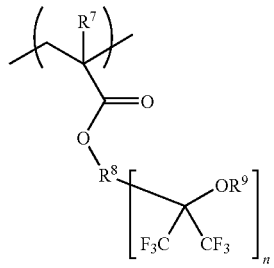

(10)

(In the above formula (10), $R^7$ represents a hydrogen atom, halogen atom, hydrocarbon group, or fluorine-containing alkyl group. $R^8$ is an alkyl group that is straight-chain or optionally branched, an alkyl group having a ring structure, an aromatic ring, or a complex substituent of them, and a part of that may be fluorinated. $R^9$ is a hydrogen atom, and a hydrocarbon group optionally branched, a fluorine-containing alkyl group, or a ring form having an aromatic or aliphatic ring, and may contain bond such as oxygen or carbonyl. Furthermore, n represents an integer of 1-2.)

Furthermore, according to the present invention, the sixth resist composition may be a seventh resist composition characterized in that the repeating unit is a repeating unit represented by the following formula (11).

[Chemical Formula 10]

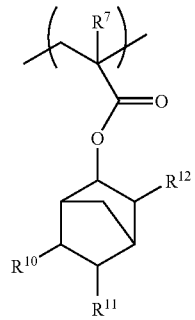

(11)

(In the above formula (11), $R^7$ is defined as in formula (10). Any one of $R^{10}$, $R^{11}$ and $R^{12}$ is $CF_3C(CF_3)(OH)CH_2$—group, the remaining two are hydrogen.)

Furthermore, according to the present invention, the sixth resist composition may be an eighth resist composition characterized in that the repeating unit is a repeating unit represented by the following formula (12).

[Chemical Formula 11]

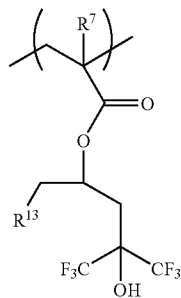

(12)

(In the above formula (12), $R^7$ has the same meaning as that of $R^7$ in formula (10). $R^{13}$ is a hydrogen atom, methyl group, ethyl group, n-propyl group, isopropyl group, n-butyl group, sec-butyl group, tert-butyl group, fluoromethyl group, difluoromethyl group, trifluoromethyl group, or perfluoroethyl group.)

Furthermore, according to the present invention, the sixth resist composition may be a ninth resist composition characterized in that the repeating unit is a repeating unit represented by the following formula (8).

[Chemical Formula 12]

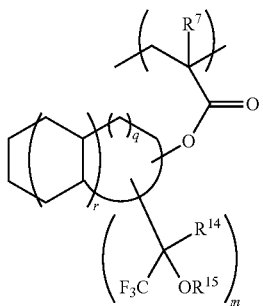

(8)

(In the above formula (8), $R^7$ has the same meaning as that of $R^7$ in formula (10). $R^{14}$ represents a methyl group or trifluoromethyl group. $R^{15}$ is a hydrogen atom, a $C_{1-25}$ straight-chain, branched or cyclic hydrocarbon group or a group containing an aromatic hydrocarbon group, and a part of that may contain fluorine atom, oxygen atom or carbonyl bond. r represents an arbitrary integer of 0-2. m and q represent arbitrary integers of 1-8, and satisfy m≦q+2. In case that $R^{14}$-$R^{15}$ are in plural number, $R^{14}$-$R^{15}$ may respectively the same or different.)

Furthermore, according to the present invention, any of the first to fourth resist compositions may be a tenth resist composition characterized in that the base resin contains a repeating unit represented by the following formula (9).

[Chemical Formula 13]

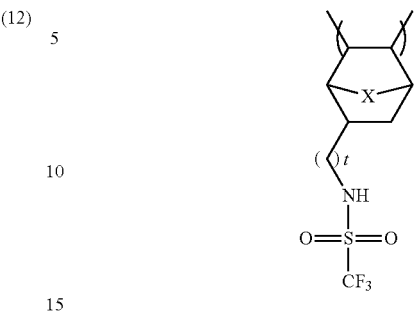

(9)

(In the above formula (9), X represents any of —$CH_2$—, —O—, and —S—. t represents an integer of 1-6.)

Furthermore, according to the present invention, there is provided a chemically amplified positive-type resist composition (en eleventh resist composition) that contains the base resin of any of the fifth to tenth resist compositions, the acid generator represented by the above formula (1), formula (6) or formula (7) and a solvent, and that the above base resin is insoluble or hardly soluble in a developing solution and becomes soluble in the developing solution by acid.

Furthermore, according to the present invention, there is provided a pattern-forming method characterized in containing the step of applying any one of the first to eleventh resist compositions on a substrate, the step of exposing to a high energy ray having a wavelength of 300 nm or less through a photomask after a heating treatment, and the step of developing using a developing solution, after a heat treatment according to need.

Furthermore, according to the present invention, the above-mentioned pattern-forming method may be characterized in that it is an immersion lithography in which an ArF excimer laser of a wavelength of 193 nm is used, and in which water is inserted between wafer and a projector lens.

DETAILED DESCRIPTION

A sulfonic acid onium salt, fluorine-containing N-sulfonyloxyimide compound or fluorine-containing oximesulfonate compound of the present invention has a good flammability and is low in human body accumulation due to a low proportion of fluorine atoms in the structure. It is sufficiently high in acidity of acid to be generated by exposure (acid to be generated is sufficiently strong) since it has two fluorine atoms at α-position of sulfo group. Furthermore, it achieves superior effects that not only can make the acid to be generated have an appropriate boiling point, but also can appropriately shorten diffusion length in the resist film and furthermore can control solubility in resist solvent and compatibility with resin by selecting a substituent on the substituted carbonyloxy group. A resist material containing the fluorine-containing sulfonic acid onium salt, fluorine-containing N-sulfonyloxyimide compound or fluorine-containing oximesulfonate compound has characteristics that resolution is superior, that line edge roughness is small, and that change of the pattern shape is small.

In the following, the best mode of embodiments of the present invention is explained. The present invention is, however, not limited to the following embodiments. It should be understood that those obtained by adding suitable changes, modifications and the like to the following embodiments, based on a normal knowledge of a person skilled in the art, are included in the scope of the present invention, to the extent of not diverging from the gist of the present invention.

[Sulfonic Acid Onium Salt, Sulfonic Acid, and Sulfonate]

A sulfonic acid onium salt of the present invention is represented by the following formula (1).

[Chemical Formula 14]

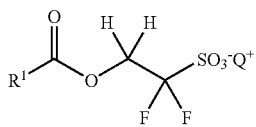

(1)

[In the above formula (1), $R^1$ has the same meaning as that of $R^1$ in formula (A).]

Herein, $R^1$ in formula (1) and formula (4) to formula (7) is specifically exemplified, as follows.

As the $C_{1-10}$ straight-chain or branched alkyl group, it is possible to mention, for example, methyl group, ethyl group, n-propyl group, i-propyl group, n-butyl group, t-butyl group, n-pentyl group, n-hexyl group, n-heptyl group, n-octyl group, n-nonyl group, n-decyl group, etc.

As the $C_{1-10}$ straight-chain or branched alkenyl group having a double bond at an end portion at least, it is possible to mention, for example, vinyl group, 1-methylethenyl group, allyl group, 3-butenyl group, 1-methylallyl group, 2-methylallyl group, 4-pentenyl group, 5-hexenyl group, etc.

As the $C_{3-20}$ alicyclic organic group, it is possible to mention, for example, cyclopentyl group, cyclohexyl group, adamantyl group, norbornyl group, campholoyl group, cyclopentylmethyl group, cyclopentylethyl group, cyclohexylmethyl group, cyclohexylethyl group, adamantylmethyl group, adamantylethyl group, norbornylmethyl group, norbornylethyl group, campholoylmethyl group, campholoylethyl group, 3-hydroxy-1-adamantyl group, 4-hydroxy-1-adamantyl group, 4-oxo-1-adamantyl group, etc.

As the $C_{6-20}$ aryl group, it is possible to mention, for example, phenyl group, o-tolyl group, m-tolyl group, p-tolyl group, p-hydroxyphenyl group, 1-naphthyl group, 1-anthracenyl, benzyl group, etc.

As the $C_{1-10}$ straight-chain or branched alkoxyl group, it is possible to mention, for example, methoxy group, ethoxy group, n-propoxy group, i-propoxy group, n-butoxy group, t-butoxy group, etc.

As the $C_{6-20}$ aryloxy group, it is possible to mention, for example, phenoxy group, p-hydroxyphenoxy group, o-tolyloxy group, m-tolyloxy group, p-tolyloxy group, etc.

As the $C_{2-10}$ straight-chain or branched alkylcarbonyl group, it is possible to mention, for example, methylcarbonyl group, ethylcarbonyl group, n-propylcarbonyl group, i-propylcarbonyl group, n-butylcarbonyl group, t-butylcarbonyl group, etc.

As the $C_{7-20}$ arylcarbonyl group, it is possible to mention, for example, phenylcarbonyl group, benzylcarbonyl group, etc.

As the $C_{2-10}$ straight-chain or branched alkylcarbonyloxy group, it is possible to mention, for example, methylcarbonyloxy group, ethylcarbonyloxy group, n-propylcarbonyloxy group, i-propylcarbonyloxy group, n-butylcarbonyloxy group, t-butylcarbonyloxy group, etc.

As the $C_{7-20}$ arylcarbonyloxy group, it is possible to mention, for example, phenylcarbonyloxy group, benzylcarbonyloxy group, etc.

As the $C_{2-10}$ straight-chain or branched alkoxycarbonyl group, it is possible to mention, for example, methoxycarbonyl group, ethoxycarbonyl group, n-propoxycarbonyl group, i-propoxycarbonyl group, n-butoxycarbonyl group, t-butoxycarbonyl group, etc.

As the $C_{7-20}$ aryloxycarbonyl group, it is possible to mention, for example, phenoxycarbonyl group, benzyloxycarbonyl group, etc.

Furthermore, hydrogen atoms on these substituents may partially or entirely be replaced with fluorine or hydroxyl group.

As $R^1$, a group of saturated hydrocarbon skeleton is particularly preferable. Specifically, the above $C_{1-10}$ straight-chain or branched alkyl group, the above $C_{3-20}$ alicyclic organic group, the above $C_{2-10}$ straight-chain or branched alkylcarbonyl group, the above $C_{2-10}$ straight-chain or branched alkylcarbonyloxy group, and the above $C_{1-10}$ straight-chain or branched alkoxycarbonyl group are preferable. Of these, the above $C_{1-10}$ straight-chain or branched alkyl group and the above $C_{3-20}$ alicyclic organic group are more preferable.

Then, $Q^+$ is explained. As mentioned above, $Q^+$ represents a sulfonium cation represented by formula (2), or an iodonium cation represented by formula (3).

As the unsubstituted $C_{1-30}$ straight-chain or branched monovalent hydrocarbon group or $C_{3-30}$ cyclic monovalent hydrocarbon group of $R^2$, $R^3$, $R^4$, $R^5$ and $R^6$ in formula (2) or formula (3), it is possible to mention, for example, alkyl group such as methyl group, ethyl group, n-propyl group, i-propyl group, n-butyl group, 1-methylpropyl group, 2-methylpropyl group, t-butyl group, n-pentyl group, i-pentyl group, 1,1-dimethylpropyl group, 1-methylbutyl group, 1,1-dimethylbutyl group, n-hexyl group, n-heptyl group, i-hexyl group, n-octyl group, i-octyl group, 2-ethylhexyl group, n-nonyl group, n-decyl group, n-undecyl group, n-dodecyl group, cyclopropyl group, cyclopentyl group, cyclohexyl group, 4-t-butylcyclohexyl group, etc., cyclohexenyl group, a group having norbornene skeleton, a group having norbornane skeleton, a group having isobornyl skeleton, a group having tricyclodecane skeleton, a group having tetracyclododecane skeleton, a group having adamantane skeleton, etc.

As a substituent of the above hydrocarbon group, it is possible to mention, for example, a $C_{6-30}$ aryl group, a $C_{2-30}$ straight-chain, branched or cyclic alkenyl group, a group, of which number of atoms is 1-30, containing a hetero atom such as halogen atom, oxygen atom, nitrogen atom, sulfur atom, phosphorus atom, silicon atom or the like, etc. These substituents can also further have arbitrary substituents, for example, at least one of the above-mentioned substituents.

As a $C_{1-30}$ straight-chain, branched or cyclic monovalent hydrocarbon group replaced with the above substituent, it is possible to mention, for example, benzyl group, methoxymethyl group, methylthiomethyl group, ethoxymethyl group, ethylthiomethyl group, phenoxymethyl group, methoxycarbonylmethyl group, ethoxycarbonylmethyl group, acetylmethyl group, fluoromethyl group, trifluoromethyl group, chloromethyl group, trichloromethyl group, 2-fluoropropyl group, (trifluoroacetyl)methyl group, (trichloroacetyl)methyl group, (pentafluorobenzoyl)methyl group, aminomethyl group, (cyclohexylamino)methyl group, (diphenylphosphino)methyl group, (trimethylsilyl)methyl group, 2-phenylethyl group, 3-phenylpropyl group, 2-aminoethyl group, etc.

Furthermore, as the unsubstituted $C_{6-30}$ aryl group of $R^2$, $R^3$, $R^4$, $R^5$ and $R^6$, it is possible to mention, for example, phenyl group, 1-naphthyl group, 2-naphthyl group, 1-anthryl group, 1-phenanthryl group, etc.

Furthermore, as the unsubstituted monovalent heterocyclic organic group, of which number of atoms is 4-30, of $R^2$, $R^3$, $R^4$, $R^5$ and $R^6$, it is possible to mention, for example, furyl group, thienyl group, pyranyl group, pyrrolyl group, thiantrenyl group, pyrazolyl group, isothiazolyl group, isoxazolyl group, pyrazinyl group, pyrimidinyl group, pyridadinyl group, tetrahydropyranyl group, tetrahydrofuranyl group, tetrahydrothiopyranyl group, tetrahydrothiofuranyl group, 3-tetrahydrothiophen-1,1-dioxide group, etc.

As a substituent of the above aryl group and the monovalent heterocyclic organic group, it is possible to mention a $C_{1-30}$ straight-chain, branched or cyclic alkyl group, a group, of which number of atoms is 1-30, containing a hetero atom such as halogen atom, oxygen atom, nitrogen atom, sulfur atom, phosphorus atom, silicon atom or the like, etc. These substituents can also further have arbitrary substituents, for example, at least one of the above substituents.

As the $C_{6-30}$ aryl group replaced with the above substituent, it is possible to mention, for example, o-tolyl group, m-tolyl group, p-tolyl group, p-hydroxyphenyl group, p-methoxyphenyl group, mesityl group, o-cumenyl, 2,3-xylyl group, 2,4-xylyl group, 2,5-xylyl group, 2,6-xylyl group, 3,4-xylyl group, 3,5-xylyl group, p-fluorophenyl group, p-trifluoromethylphenyl group, p-chlorophenyl group, p-bromophenyl group, p-iodophenyl group, etc.

As the monovalent heterocyclic organic group, of which number of atoms is 4-30, replaced with the above substituent, it is possible to mention, for example, 2-bromofuryl group, 3-methoxythienyl group, 3-bromotetrahydropyranyl group, 4-methoxytetrahydropyranyl group, 4-methoxytetrahydrothiopyranyl group, etc.

The monovalent sulfonium ion represented by formula (2) is specifically exemplified by trimethylsulfonium ion, tributylsulfonium ion, dimethyl(2-oxocyclohexyl)sulfonium ion, bis(2-oxocyclohexyl)methylsulfonium ion, (10-camphenoyl)methyl(2-oxocyclohexypsulfonium ion, (2-norbornyl)methyl(2-oxocyclohexyl)sulfonium ion, triphenylsulfonium ion, diphenyltolylsulfonium ion, diphenylxylylsulfonium ion, mesityldiphenylsulfonium ion, (t-butylphenyl)diphenylsulfonium ion, (octylphenyl)diphenylsulfonium ion, (cyclohexylphenyl)diphenylsulfonium ion, biphenyldiphenylsulfonium ion, (hydroxymethylphenyl)diphenylsulfonium ion, (methoxymethylphenyl)diphenylsulfonium ion, (acetylphenyl)diphenylsulfonium ion, (benzoylphenyl)diphenylsulfonium ion, (hydroxycarbonylphenyl)diphenylsulfonium ion, (methoxycarbonylphenyl)diphenylsulfonium ion, (trifluoromethylphenyl)diphenylsulfonium ion, (fluorophenyl)diphenylsulfonium ion, (chlorophenyl)diphenylsulfonium ion, (bromophenyl)diphenylsulfonium ion, (iodophenyl)diphenylsulfonium ion, pentafluorophenyldiphenylsulfonium ion, (hydroxyphenyl)diphenylsulfonium ion, (methoxyphenyl)diphenylsulfonium ion, (butoxyphenyl)diphenylsulfonium ion, (acetyloxyphenyl)diphenylsulfonium ion, (benzoyloxyphenyl)diphenylsulfonium ion, (dimethylcarbamoylphenyl)diphenylsulfonium ion, (acetylamidophenyl)diphenylsulfonium ion, phenylditolylsulfonium ion, phenyldixylylsulfonium ion, dimesitylphenylsulfonium ion, bis(t-butylphenyl)phenylsulfonium ion, bis(octylphenyl)phenylsulfonium ion, bis(cyclohexylphenyl)phenylsulfonium ion, dibiphenylphenylsulfonium ion, bis(hydroxymethylphenyl)phenylsulfonium ion, bis(methoxymethylphenyl)phenylsulfonium ion, bis(acetylphenyl)phenylsulfonium ion, bis(benzoylphenyl)phenylsulfonium ion, bis(hydroxycarbonylphenyl)phenylsulfonium ion, bis(methoxycarbonylphenyl)phenylsulfonium ion, bis(trifluoromethylphenyl)phenylsulfonium ion, bis(fluorophenyl)phenylsulfonium ion, bis(chlorophenyl)phenylsulfonium ion, bis(bromophenyl)phenylsulfonium ion, bis(iodophenyl)phenylsulfonium ion, dipentafluorophenylphenylsulfonium ion, bis(hydroxyphenyl)phenylsulfonium ion, bis(methoxyphenyl)phenylsulfonium ion, bis(butoxyphenyl)phenylsulfonium ion, bis(acetyloxyphenyl)phenylsulfonium ion, bis(benzoyloxyphenyl)phenylsulfonium ion, bis(dimethylcarbamoylphenyl)phenylsulfonium ion, bis(acetylamidophenyl)phenylsulfonium ion, tristolylsulfonium ion, trisxylylsulfonium ion, trismesitylphenylsulfonium ion, tris(t-butylphenyl)sulfonium ion, tris(octylphenyl)sulfonium ion, tris(cyclohexylphenyl)sulfonium ion, tribiphenylsulfonium ion, tris(hydroxymethylphenyl)sulfonium ion, tris(methoxymethylphenyl)sulfonium ion, tris(acetylphenyl)sulfonium ion, tris(benzoylphenyl)sulfonium ion, tris(hydroxycarbonylphenyl)sulfonium ion, tris(methoxycarbonylphenyl)sulfonium ion, tris(trifluoromethylphenyl)sulfonium ion, tris(fluorophenyl)sulfonium ion, tris(chlorophenyl)sulfonium ion, tris(bromophenyl)sulfonium ion, tris(iodophenyl)sulfonium ion, dipentafluorophenylsulfonium ion, tris(hydroxyphenyl)sulfonium ion, tris(methoxyphenyl)sulfonium ion, tris(butoxyphenyl)sulfonium ion, tris(acetyloxyphenyl)sulfonium ion, tris(benzoyloxyphenyl)sulfonium ion, tris(dimethylcarbamoylphenyl)sulfonium ion, tris(acetylamidophenyl)sulfonium ion, methyldiphenylsulfonium ion, ethyldiphenylsulfonium ion, butyldiphenylsulfonium ion, hexyldiphenylsulfonium ion, octyldiphenylsulfonium ion, cyclohexyldiphenylsulfonium ion, 2-oxocyclohexyldiphenylsulfonium ion, norbornyldiphenylsulfonium ion, camphenoyldiphenylsulfonium ion, pinanoyldiphenylsulfonium ion, naphthyldiphenylsulfonium ion, antranyldiphenylsulfonium ion, benzyldiphenylsulfonium ion, trifluoromethyldiphenylsulfonium ion, methoxycarbonylmethyldiphenylsulfonium ion, butoxycarbonylmethyldiphenylsulfonium ion, benzoylmethyldiphenylsulfonium ion, (methylthiophenyl)diphenylsulfonium ion, (phenylthiophenyl)diphenylsulfonium ion, (acetylphenylthiophenyl)diphenylsulfonium ion, dimethylphenylsulfonium ion, diethylphenylsulfonium ion, dibutylphenylsulfonium ion, dihexylphenylsulfonium ion, dioctylphenylsulfonium ion, dicyclohexylphenylsulfonium ion, bis(2-oxocyclohexyl)phenylsulfonium ion, dinorbornylphenylsulfonium ion, dicamphenoylphenylsulfonium ion, dipinanoylphenylsulfonium ion, dinaphthylphenylsulfonium ion, dibenzylphenylsulfonium ion, trifluoromethyldiphenylsulfonium ion, bis(methoxycarbonylmethyl)phenylsulfonium ion, bis(butoxycarbonylmethyl)phenylsulfonium ion, dibenzoylmethylphenylsulfonium ion, bis(methylthiophenyl)phenylsulfonium ion, bis(phenylthiophenyl)phenylsulfonium ion, bis(acetylphenylthiophenyl)phenylsulfonium ion, dimethyl(2-oxocyclohexyl)sulfonium ion, bis(2-oxocyclohexyl)methylsulfonium ion, (10-camphenoyl)methyl(2-oxocyclohexyl)sulfonium ion, (2-norbornyl)methyl(2-oxocyclohexyl)sulfonium ion, triethylsulfonium ion, dihexylmethylsulfonium ion, trioctylsulfonium ion, dicyclohexylethylsulfonium ion, methyltetrahydrothiophenium ion, triphenyloxosulfonium ion, etc.

The monovalent iodonium ion represented by formula (3) is specifically exemplified by diphenyliodonium ion, bis-(t-butylphenyl)iodonium ion, (methoxyphenyl)phenyliodonium ion, (butoxyphenyl)phenyliodonium ion, trifluoroethylphenyliodonium ion, pentafluorophenylphenyliodonium ion, etc.

Of these monovalent onium ions, triphenylsulfonium ion, diphenyltolylsulfonium ion, mesityldiphenylsulfonium ion, tristolylsulfonium ion, tris(t-butylphenyl)sulfonium ion, tris(methoxyphenyl)sulfonium ion, (hydroxyphenyl)diphenylsulfonium ion, diphenyliodonium ion, bis-(t-butylphenyl)iodonium ion, and the like are preferable, and triphenylsulfonium ion is particularly preferable.

The fluorine-containing sulfonic acid of the present invention is represented by the following formula (4).

[Chemical Formula 15]

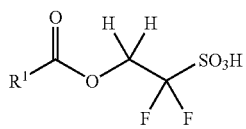

(4)

The resist composition of the present invention contains base resin, acid generator, and solvent. In this case, as the acid generator, one that generates a fluorine-containing sulfonic acid represented by the above formula (4), when it is irradiated with an active radiation of a wavelength of 200 nm or less, is preferably used. As the acid generator, it is possible to preferably use a fluorine-containing sulfonic acid onium salt represented by the above formula (1).

(In the above formula (4), $R^1$ has the same meaning as that of $R^1$ in formula (A).)

$R^1$ can specifically and similarly be exemplified by the above-mentioned ones.

The fluorine-containing sulfonate of the present invention is represented by the following formula (5).

[Chemical Formula 16]

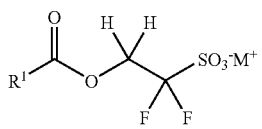

(5)

(In the above formula (5), $R^1$ has the same meaning as that of $R^1$ in formula (A). $M^+$ represents a monovalent cation.)

$R^1$ can specifically and similarly be exemplified by the above-mentioned ones. M+ can specifically be exemplified by lithium ion, sodium ion, potassium ion, ammonium ion or tetramethylammonium ion, etc. Of these, lithium ion, sodium ion, and potassium ion, which are metal ions, are preferable. Sodium ion is particularly preferable.

The amount of the fluorine-containing sulfonic acid onium salt contained in a resist composition of the present invention is preferably in a range of 0.2-15 parts by weight relative to 100 parts by weight of the base resin. More preferably, it can be added in a range of 1-10 parts by weight.

It is possible to produce the fluorine-containing sulfonic acid onium salt represented by formula (1), for example, by the following reaction scheme 1.

[Reaction Scheme 1]

[Chemical Formula 17]

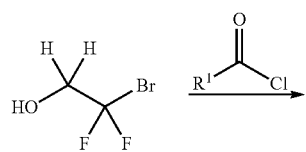

-continued

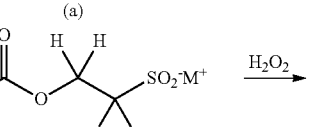
(a)

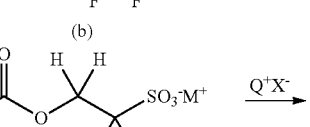
(b)

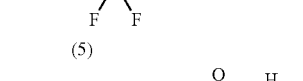
(5)

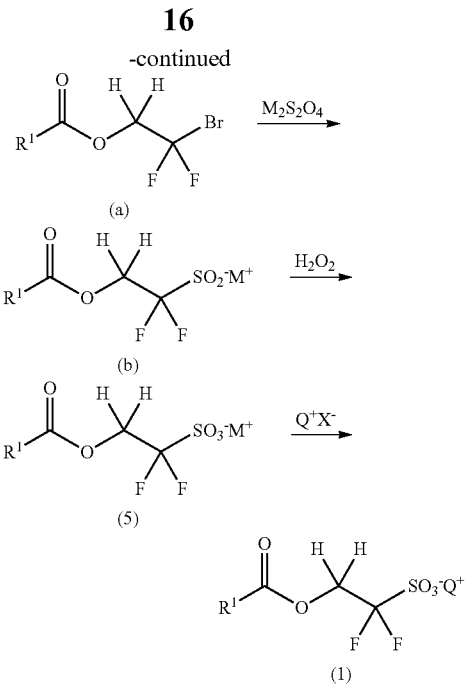
(1)

That is, the first step is a step for obtaining a fluorine-containing brominated ester represented by formula (a) by reacting 2-bromo-2,2-difluoroethanol with various carboxylic chlorides.

The second step is a step for obtaining a fluorine-containing sulfinate represented by formula (b) by sulfinating the fluorine-containing brominated ester represented by formula (a), which has been obtained by the first step, by using a sulfinating agent such as hydrosulfite or the like.

The third step is a step for obtaining a fluorine-containing sulfonate represented by formula (5) by oxidizing the fluorine-containing sulfinate represented by formula (b), which has been obtained by the second step, by using an oxidizing agent such as hydrogen peroxide or the like.

The fourth step is a step for obtaining a fluorine-containing sulfonic acid onium salt represented by formula (1) by reacting the fluorine-containing sulfonate represented by formula (5), which has been obtained by the third step, with a monovalent onium salt represented by formula $Q^+X^-$. It is the production process comprising the four steps.

[N-sulfonyloxyimide Compound]

The fluorine-containing N-sulfonyloxyimide compound of the present invention is represented by the following formula (6). This compound can also preferably be used as an acid generator that generates the above-mentioned fluorine-containing sulfonic acid represented by formula (4).

[Chemical Formula 18]

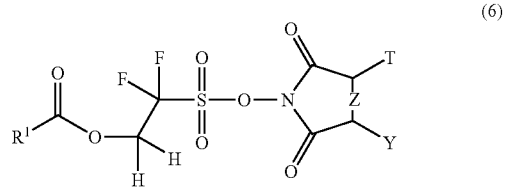

(6)

(In the above formula (6), $R^1$ has the same meaning as that of $R^1$ in formula (A). Z shows a single bond, double bond, methylene group or oxygen atom. T and Y independently show hydrogen atoms or $C_{1-10}$ substituted or unsubstituted alkyl groups, or T and Y jointly may form an alicyclic structure, aromatic ring structure or hetero ring structure by including carbon atoms to which they are attached.)

$R^1$ can specifically and similarly be exemplified by the above-mentioned ones. As the $C_{1-10}$ unsubstituted alkyl group, it is possible to mention, for example, methyl group, ethyl group, n-propyl group, i-propyl group, n-butyl group, t-butyl group, n-pentyl group, n-hexyl group, n-heptyl group, n-octyl group, n-nonyl group, n-decyl group, etc. The substituted alkyl group can be exemplified by those in which hydrogen atoms on the above-mentioned unsubstituted alkyl group have partially or entirely been replaced with fluorine or hydroxyl group, or those in which two hydrogen atoms on the same carbon, which constitutes the above-mentioned unsubstituted alkyl group, have been replaced with one oxygen atom, resulting in a keto group.

For example, examples of alicyclic structures, aromatic ring structures and hetero ring structures, which are formed by T and Y jointly by including carbon atoms to which they are attached have ones mentioned by the following formulas (they are shown as the right-side portion of formula (6)).

[Chemical Formula 19]

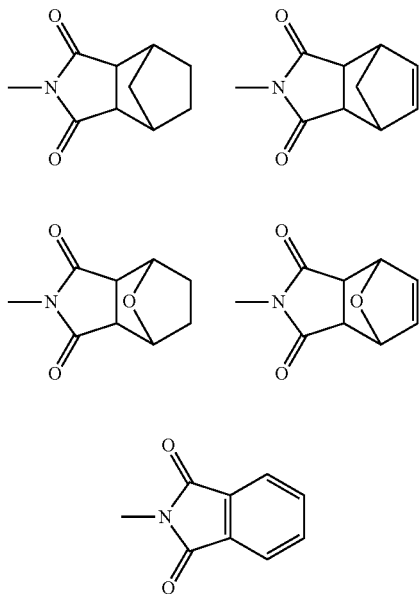

[Chemical Formula 20]

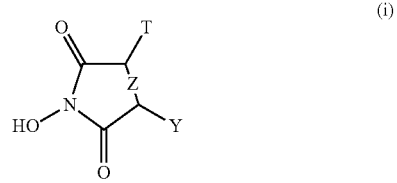

(i)

(In the formula, Z shows a single bond, double bond, methylene group or oxygen atom. T and Y independently show hydrogen atoms or $C_{1-10}$ substituted or unsubstituted alkyl groups, or T and Y jointly may form an alicyclic structure, aromatic ring structure or hetero ring structure by including carbon atoms to which they are attached.)

and the above-mentioned sulfonyl chloride are dissolved in a solvent such as THF, dichloromethane or the like, following by reacting under a basic condition or reacting in a basic solvent such as triethylamine or pyridine. With this, it is possible to obtain the target fluorine-containing N-sulfonyloxyimide compound represented by formula (6) ([Reaction Scheme 2]).

[Reaction Scheme 2]

[Chemical Formula 21]

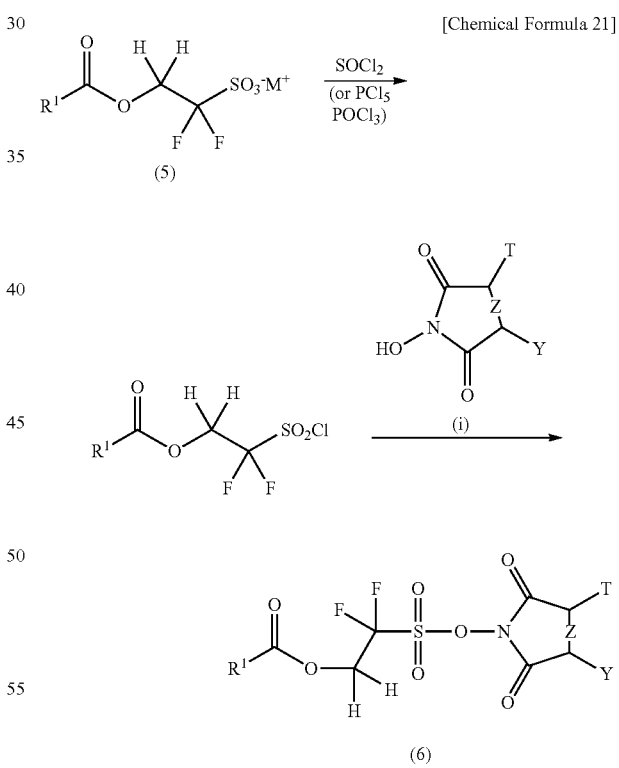

The amount of the fluorine-containing N-sulfonyloxyimide compound contained in a resist composition of the present invention is preferably in a range of 0.2-15 parts by weight relative to 100 parts by weight of the base resin. More preferably, it can be added in a range of 1-10 parts by weight.

Then, the process for synthesizing the fluorine-containing N-sulfonyloxyimide compounds represented by formula (6) is explained. The process for synthesizing these compounds can be based on Japanese Patent Publication No. 2001-199955 and the like. Specifically, a sulfonate represented by formula (5) is converted to a sulfonyl chloride by using phosphorus pentachloride, thionyl chloride, phosphorus oxychloride, or the like.

Then, N-hydroxydicarboxylmide represented by formula (1), which is on the market or has been synthesized from the corresponding dicarboxylic acid and hydroxylamine

[Oximesulfonate Compound]

The fluorine-containing oximesulfonate compound of the present invention is represented by the following formula (7). The fluorine-containing oximesulfonate compound can also be used as an acid generator that generates the above-mentioned fluorine-containing sulfonic acid represented by formula (4).

[Chemical Formula 22]

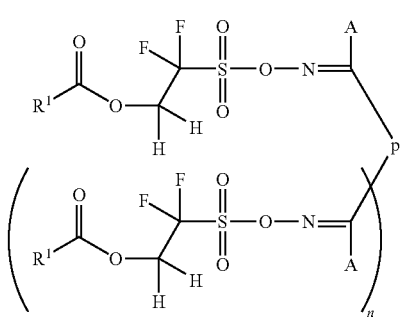

(In the above formula (7), $R^1$ has the same meaning as that of $R^1$ in formula (A). n represents 0 or 1. In case that n is 0, p represents a substituted or unsubstituted $C_{1-20}$ alkyl group, or substituted or unsubstituted $C_{6-15}$ aryl group. In case that n is 1, p represents a single bond, substituted or unsubstituted $C_{1-20}$ alkylene group, or substituted or unsubstituted $C_{6-15}$ arylene group. A represents a cyano group, trifluoromethyl group, perfluoroethyl group, perfluoropropyl group, 5H-perfluoropentyl group, 6H-perfluorohexyl group, nitro group or methyl group. In case that n is 1, both of A may be attached to each other, thereby forming a $C_6$ ring together with carbon atoms to which they are attached.)

$R^1$ can specifically and similarly be exemplified by the above-mentioned ones. Skeleton of these oximesulfonates can be based on, for example, one disclosed in International Publication No. 2004/074242.

The amount of the fluorine-containing oximesulfonate compound contained in the resist composition of the present invention is preferably in a range of 0.2-15 parts by weight, relative to 100 parts by weight of the base resin. More preferably, it can be added in a range of 1-10 parts by weight.

Then, the process for synthesizing the oximesulfonate compounds represented by formula (7) is explained. The process for synthesizing these compounds can be based on the above-mentioned patent publication and the like. Specifically, a sulfonate represented by formula (5) is converted to a sulfonyl chloride by using phosphorus pentachloride, thionyl chloride, phosphorus oxychloride, or the like.

Then, an oxime represented by formula (ii), which is on the market or has been synthesized from the corresponding ketone and hydroxylamine

[Chemical Formula 23]

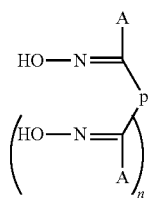

(In the formula, n represents 0 or 1. In case that n is 0, p represents a substituted or unsubstituted $C_{1-20}$ alkyl group, or substituted or unsubstituted $C_{6-15}$ aryl group. In case that n is 1, p represents a single bond, substituted or unsubstituted $C_{1-20}$ alkylene group, or substituted or unsubstituted $C_{6-15}$ arylene group. A represents a cyano group, trifluoromethyl group, perfluoroethyl group, perfluoropropyl group, 5H-perfluoropentyl group, 6H-perfluorohexyl group, nitro group or methyl group. In case that n is 1, both of A may be attached to each other, thereby forming a $C_6$ ring together with carbon atoms to which they are attached.) and the above-mentioned sulfonyl chloride are dissolved in a solvent such as THF, dichloromethane or the like, following by reacting under a basic condition or reacting in a basic solvent such as triethylamine or pyridine. With this, it can be obtained ([Reaction Scheme 3]).

[Reaction Scheme 3]

[Chemical Formula 24]

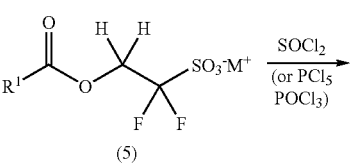

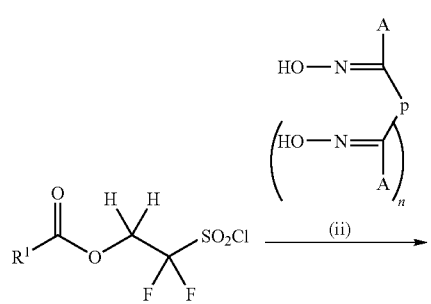

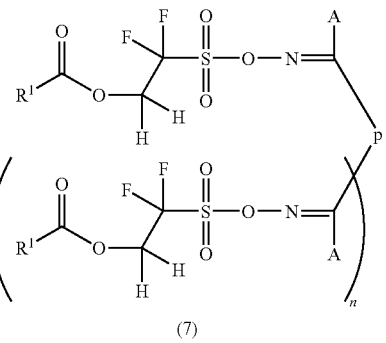

[Acid Generator and Sulfonic Acid]

It is possible to generate the fluorine-containing sulfonic acid represented by formula (4) of the present invention by irradiating the fluorine-containing sulfonic acid onium salt represented by formula (1), the fluorine-containing N-sulfonyloxyimide compound represented by formula (6), or the fluorine-containing oximesulfonate compound represented by formula (7) with an active radiation, particularly KrF excimer laser, ArF excimer laser, or far ultraviolet radiation represented by EUV, electron beam, etc. ([Reaction Scheme 4]).

[Reaction Scheme 4]

[Chemical Formula 25]

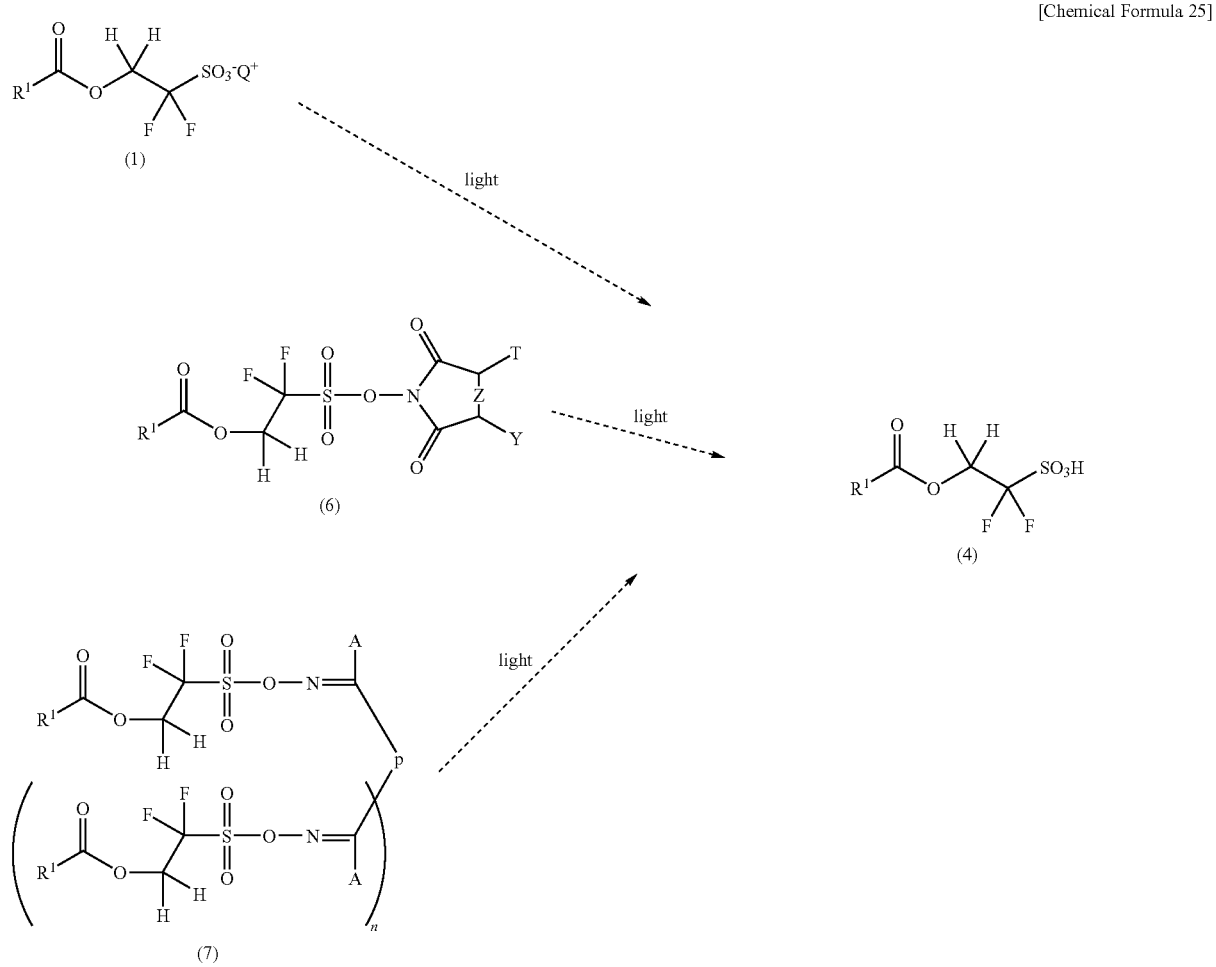

Therefore, the fluorine-containing sulfonic acid onium salt represented by formula (1), the fluorine-containing N-sulfonyloxyimide compound represented by formula (6), or the fluorine-containing oximesulfonate compound represented by formula (7) can be used as a photoacid generator.

The photoacid generator of the present invention contains as an effective component the fluorine-containing sulfonic acid onium salt represented by formula (1), the fluorine-containing N-sulfonyloxyimide compound represented by formula (6), or the fluorine-containing oximesulfonate compound represented by formula (7). A photosensitive resin composition (resist material) is formed and can serve for use by mixing the photoacid generator of the present invention with a base resin (a photosensitive resin) that changes solubility in alkali developing solution by an action of acid. {In general, simple substance (solid) of the above fluorine-containing sulfonic acid onium salt is used alone as "photoacid generator" or by blending into a photosensitive resin together with another photoacid generator.}

As the polymer compound is exemplified, the first example is a positive-type resist that changes into a polymer compound having an acidic unit soluble in developing solution, such as carboxylic acid, phenol or hexafluoroalcohol, by irradiation with light or active energy ray to convert the photoacid generator according to the present invention into a strong acid (fluorine-containing sulfonic acid represented by formula (4)) and by allowing a protective group of the polymer side chain to leave by an action of the strong acid, and the second example is a negative-type resist that becomes insoluble in developing solution by irradiation with light or electron beam to convert the photoacid generator according to the present invention into a strong acid and by a reaction of a functional group of the polymer side chain with a crosslinking agent, which has previously been mixed, by an action of the strong acid. They can widely be applied to various photosensitive compositions.

That is, the type of the polymer compound preferably used in the present invention can be exemplified without a particular limitation by a polymer or copolymer of hydroxystyrene or protected hydroxystyrene, a hexafluorocarbinol-containing, styrene-series polymer or copolymer, a polymer or copolymer of methacrylic acid or protected methacrylate, a polymer or copolymer of acrylic acid or protected acrylate, a polymer or copolymer of α-trifluoromethylacrylic acid or protected α-trifluoromethylacrylate, a polymer or copolymer of an acrylate or methacrylate having hexafluorocarbinol at its side chain, a norbornene polymer or copolymer having carboxylic acid or hexafluorocarbinol, and the like.

The photoacid generator of the present invention can be used in a range of 0.2-15 parts relative to 100 parts by weight of the polymer compound. More preferably, it can be added in a range of 1-10 parts by weight. Besides adding the photoacid generator according to the present invention to the polymer compound, it is also possible to add various additives such as amine-series compounds, quencher, surfactant, surface modifier, curing agent, curing accelerator, dissolution accelerator and the like. Furthermore, it can also be used in combination with another photoacid generator.

Wavelength of the light or active energy ray usable in the present invention is not particularly limited. Preferably, it can preferably be applied to ultraviolet rays such as g-line and i-line, 248 nm of KrF excimer laser, 193 nm of ArF excimer laser, 157 nm of F2 laser, or 13 nm that is EUV of extreme ultraviolet rays, or the like.

It can be used in not only lithography used in normal atmospheric environment, but also in immersion lithography in which a liquid such as water or solvent is brought into contact with a resist film or a protective film (top coat) applied onto a resist film, and it is irradiated with light or active electron beam through the liquid.

The sulfonic acid onium salt of formula (1), the fluorine-containing sulfonic acid of formula (4), the fluorine-containing sulfonate of formula (5), the fluorine-containing N-sulfonyloxyimide compound of formula (6), and the fluorine-containing oximesulfonate compound represented by formula (7) of the present invention are each novel compounds not yet published in publications.

[Base Resin]

Then, we explain a base resin added to a resist composition according to the present invention. As the base resin, a repeating unit containing no aromatic substituent is used preferably. It is preferably a polymer obtained by polymerizing one kind of monomer selected from the group consisting of olefins, fluorine-containing olefins, acrylates, methacrylates, fluorine-containing acrylates, fluorine-containing methacrylates, norbornene compounds, fluorine-containing norbornene compounds, styrene-series compounds, fluorine-containing styrene-series compounds, vinyl ethers, and fluorine-containing vinyl ethers, or a copolymer obtained by copolymerizing at least two kinds of the above-mentioned monomers.

The olefins can be exemplified by ethylene, propylene, etc. The fluoroolefins can be exemplified by vinyl fluoride, vinylidene fluoride, trifluoroethylene, chlorotrifluoroethylene, tetrafluoroethylene, hexafluoropropylene, hexafluoroisobutene, etc.

Furthermore, the acrylates or methacrylates can be used without a particular limitation in terms of ester side chain. As they are exemplified by known compounds, it is possible to use alkyl esters of acrylic acid or methacrylic acid such as methyl acrylate or methacrylate, ethyl acrylate or methacrylate, n-propyl acrylate or methacrylate, isopropyl acrylate or methacrylate, n-butyl acrylate or methacrylate, isobutyl acrylate or methacrylate, n-hexyl acrylate or methacrylate, n-octyl acrylate or methacrylate, 2-ethylhexyl acrylate or methacrylate, lauryl acrylate or methacrylate, 2-hydroxyethyl acrylate or methacrylate, 2-hydroxypropyl acrylate or methacrylate, etc., acrylates or methacrylates containing ethylene glycol, propylene glycol or tetramethylene glycol group, unsaturated amides such as acrylamide, methacrylamide, N-methylol acrylamide, N-methylol methacrylamide, diacetone acrylamide, etc., vinyl silanes and acrylic or methacrylic esters containing acrylonitrile, methacrylonitrile or alkoxysilane, t-butyl acrylate or methacrylate, 3-oxocyclohexyl acrylate or methacrylate, adamantyl acrylate or methacrylate, alkyladamantyl acrylate or methacrylate, cyclohexyl acrylate or methacrylate, tricyclodecanylacrylate or methacrylate, an acrylate or methacrylate containing a ring structure such as lactone ring or norbornene ring, acrylic acid, methacrylic acid, etc. Furthermore, it is also possible to use the above-mentioned acrylate compounds containing a cyano group, and as analogous compounds maleic acid, fumaric acid, maleic anhydride, etc.

Furthermore, the fluorine-containing acrylate or fluorine-containing methacrylate is an acrylate or methacrylate having a group having a fluorine atom at α-position or ester moiety, and a cyano group may be introduced into α-position. For example, as the monomer having a fluorine-containing alkyl group introduced into α-position, there is preferably used a monomer in which α-position is provided with a trifluoromethyl group, trifluoroethyl group, nonafluoro-n-butyl group or the like.

On the other hand, they are acrylates or methacrylates, in which their ester moiety is a fluorine alkyl group that is a perfluoroalkyl group or fluoroalkyl group, or a unit in which a cyclic structure and fluorine are coexistent in the ester moiety, and which have a unit in which the cyclic structure has, for example, a fluorine-containing benzene ring, a fluorine-containing cyclopentane ring, a fluorine-containing cyclohexane ring, a fluorine-containing cycloheptane ring or the like, in which fluorine or trifluoromethyl group has been substituted therefor. Furthermore, it is also possible to use an acrylic or methacrylic acid ester of which ester moiety is a fluorine-containing t-butyl ester group, etc. Of such units, as particularly representative ones are exemplified in the form of monomer, it is possible to cite 2,2,2-trifluoroethyl acrylate, 2,2,3,3-tetrafluoropropyl acrylate, 1,1,1,3,3,3-hexafluoroisopropyl acrylate, heptafluoroisopropyl acrylate, 1,1-dihydroheptafluoro-n-butyl acrylate, 1,1,5-trihydrooctafluoro-n-pentyl acrylate, 1,1,2,2-tetrahydrotridecafluoro-n-octyl acrylate, 1,1,2,2-tetrahydroheptadecafluoro-n-decyl acrylate, 2,2,2-trifluoroethyl methacrylate, 2,2,3,3-tetrafluoropropyl methacrylate, 1,1,1,3,3,3-hexafluoroisopropyl methacrylate, heptafluoroisopropyl methacrylate, 1,1-dihydroheptafluoro-n-butyl methacrylate, 1,1,5-trihydrooctafluoro-n-pentyl methacrylate, 1,1,2,2-tetrahydrotridecafluoro-n-octyl methacrylate, 1,1,2,2-tetrahydroheptadecafluoro-n-decyl methacrylate, perfluorocyclohexylmethyl acrylate, perfluorocyclohexylmethyl methacrylate, etc.

The norbornene compounds and the fluorine-containing norbornene compounds are norbornene monomers having a single or plurality of nucleus structures, and these can be used without a particular limitation. Upon this, norbornene compounds are preferably used, that have been obtained by conducting Diels Alder addition reactions by using unsaturated compounds such as allyl alcohol, fluorine-containing allyl alcohol, acrylic acid, α-fluoroacrylic acid, methacrylic acid, and all of the acrylates or methacrylates and fluorine-containing acrylates or methacrylates mentioned in the present specification, and cyclopentadiene or cyclohexadiene.

Furthermore, it is also possible to use styrene-series compounds, fluorine-containing styrene-series compounds, vinyl ethers, fluorine-containing vinyl ethers, allyl ethers, vinyl esters, vinyl silanes, etc. Herein, as styrene-series compounds and fluorine-containing styrene-series compounds, it is possible to use, besides styrene, fluorinated styrene, hydroxystyrene, etc., hexafluoroacetone-added styrene-series compounds, styrene or hydroxystyrene having trifluoromethyl group substituted for hydrogen, the above-mentioned styrene or fluorine-containing styrene-series compound in which halogen, alkyl group or fluorine-containing alkyl group is attached to α-position, etc. On the other hand, it is also possible to use vinyl ethers, fluorine-containing vinyl ethers, allyl ethers, vinyl esters, etc. For example, they are alkyl vinyl ethers optionally containing methyl group, ethyl group, and hydroxy group such as hydroxyethyl group or hydroxybutyl group, and their hydrogen may partially or entirely be replaced with fluorine. Furthermore, it is also possible to use cyclohexyl vinyl ethers, cyclic-type vinyl ethers having hydrogen or carbonyl bond in their cyclic structure, and monomers in which hydrogen of those cyclic-type vinyl ethers has partially or entirely been replaced with fluorine. Furthermore, it is also possible to use allyl ethers, vinyl esters and vinyl silanes without a particular limitation, as long as they are publicly known compounds.

Of the above-mentioned base resins, particularly there is preferably used a base resin containing a repeating unit represented by the following formula (10).

[Chemical Formula 26]

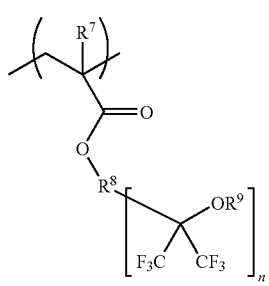

(10)

In the above formula (10), $R^7$ represents a hydrogen atom, halogen atom, hydrocarbon group, or fluorine-containing alkyl group. $R^8$ is an alkyl group that is straight-chain or optionally branched, an alkyl group having a cyclic structure, an aromatic ring, or a complex substituent of them, and a part of that may be fluorinated. $R^9$ is a hydrogen atom, and a hydrocarbon group optionally branched, a fluorine-containing alkyl group, or a cyclic form having an aromatic or aliphatic ring, and may contain bond such as oxygen or carbonyl. Furthermore, n represents an integer of 1-2.

$R^7$ usable in formula (10) can be used without a particular limitation, as long as it is a hydrogen atom, halogen atom, hydrocarbon group, or fluorine-containing alkyl group. As preferable substituents are exemplarily shown, the halogen atom can be exemplified by fluorine, chlorine, bromine, etc. Furthermore, the hydrocarbon group can be exemplified by methyl group, ethyl group, propyl group, isopropyl group, butyl group, isobutyl group, sec-butyl group, tert-butyl group, cyclopentyl group, cyclohexyl group, phenyl group, benzyl group, phenethyl group, etc. Furthermore, the fluorine-containing alkyl group can be exemplified by those in which hydrogen atoms of the alkyl group have partially or entirely been replaced with halogen atom. However, the number of carbons in the case of the hydrocarbon group and the fluorine-containing alkyl group is preferably around 1-20. Furthermore, in view of polymerizability, the number of carbons of 1-4 is preferably used. In particular, as the fluorine-containing alkyl group is exemplified, it can be exemplified by trifluoromethyl group of —$CF_3$, trifluoroethyl group of —$CH_2CF_3$, 1,1,1,3,3,3-hexafluoroisopropyl group, heptafluoroisopropyl group, nonafluoro-n-butyl group of —$C_4F_9$, etc.

Furthermore, $R^8$ usable in formula (10) is an alkyl group that is straight-chain or optionally branched, an alkyl group having a cyclic structure, an aromatic ring, or a complex substituent of them, and a part of that may be fluorinated and may contain an unsaturated bond. Without limitation in structure, it is possible to use, for example, a straight-chain or branched alkylene group such as methylene, ethylene, isopropylene, t-butylene or the like, a cyclic structure containing cyclobutene, cyclohexane, norbornene, adamantane group or the like, phenyl group, etc. As preferable structures, repeating units represented by the following formulas (11), (12) and (8) can be shown as examples.

[Chemical Formula 27]

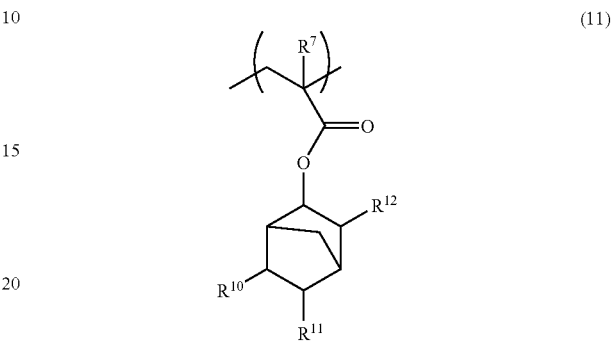

(11)

[Chemical Formula 28]

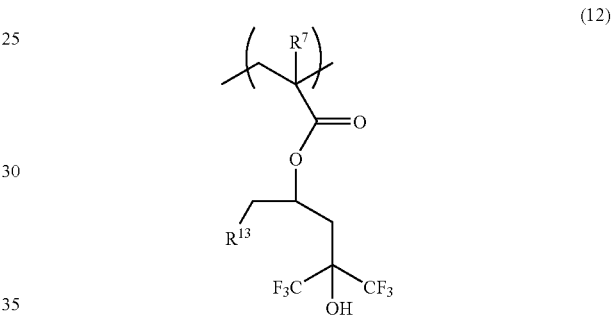

(12)

[Chemical Formula 29]

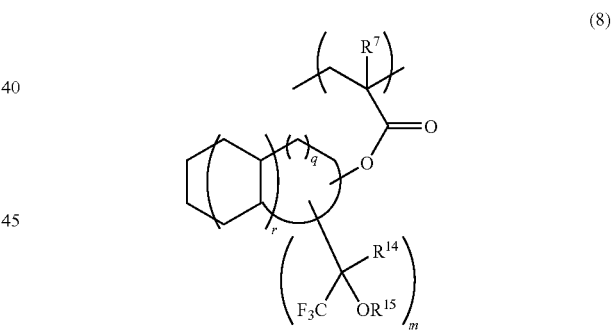

(8)

In formula (11), $R^7$ is defined as in formula (10). Any one of $R^{10}$, $R^{11}$ and $R^{12}$ is $CF_3C(CF_3)(OH)CH_2$— group, and the remaining two are hydrogen. In formula (12), $R^7$ has the same meaning as that of $R^7$ in formula (10). $R^{13}$ is a hydrogen atom, methyl group, ethyl group, n-propyl group, isopropyl group, n-butyl group, sec-butyl group, tert-butyl group, fluoromethyl group, difluoromethyl group, trifluoromethyl group, or perfluoroethyl group. In formula (8), $R^7$ has the same meaning as that of $R^7$ in formula (10). $R^{14}$ represents a methyl group or trifluoromethyl group. $R^{15}$ is a hydrogen atom, a $C_{1-25}$ straight-chain, branched or cyclic hydrocarbon group or a group containing an aromatic hydrocarbon group, and a part of that may contain fluorine atom, oxygen atom or carbonyl bond. r represents an arbitrary integer of 0-2. m and q represent arbitrary integers of 1-8, and satisfy $m \leq q+2$. In case that $R^{14}$-$R^{15}$ are in plural number, $R^{14}$-$R^{15}$ may respectively the same or different.

A $C_{1-25}$ straight-chain, branched or cyclic hydrocarbon group or an aromatic hydrocarbon group, which is usable as $R^{15}$ in formula (8), can be exemplified by methyl group, ethyl group, propyl group, isopropyl group, cyclopropyl group, n-propyl group, sec-butyl group, tert-butyl group, n-pentyl group, cyclopentyl group, sec-pentyl group, neopentyl group, hexyl group, cyclohexyl group, ethylhexyl group, norbornel group, adamantyl group, vinyl group, allyl group, butenyl group, pentenyl group, ethynyl group, phenyl group, benzyl group, 4-methoxybenzyl group, etc., and those in which the above functional groups have partially or entirely been replaced with fluorine atom are also fine. Furthermore, as those having oxygen atom, it is possible to mention alkoxycarbonyl group, acetal group, acyl group, etc. The alkoxycarbonyl group can be exemplified by tert-butoxycarbonyl group, tert-amyloxycarbonyl group, methoxycarbonyl group, ethoxycarbonyl group, i-propoxycarbonyl group, etc. As the acetal group, it is possible to mention chain-like ethers of methoxymethyl group, methoxyethoxymethyl group, ethoxyethyl group, butoxyethyl group, cyclohexyloxyethyl group, benzyloxyethyl group, phenethyloxyethyl group, ethoxypropyl group, benzyloxypropyl group, phenethyloxypropyl group, ethoxybutyl group and ethoxyisobutyl group, and cyclic ethers such as tetrahydrofuranyl group and tetrahydropyranyl group. As the acyl group, it is possible to mention acetyl group, propionyl group, butyryl group, heptanoyl group, hexanoyl group, valeryl group, pivaloyl group, isovaleryl group, lauryloyl group, myristoyl group, palmytoyl group, stearoyl group, oxalyl group, malonyl group, succinyl group, glutaryl group, adipoyl group, piperoyl group, suberoyl group, azelaoyl group, sebacoyl group, acryloyl group, propioloyl group, methacryloyl group, crotonoyl group, oleoyl group, maleoyl group, fumaroyl group, mesaconoyl group, campholoyl group, benzoyl group, phthaloyl group, isophthaloyl group, terephthaloyl group, naphthoyl group, toluoyl group, hydratoropoyl group, atoropoyl group, cinnamoyl group, furoyl group, thenoyl group, nicotinoyl group, isonicotinoyl group, etc. Furthermore, it is also possible to use those in which hydrogen atoms of the above substituents have partially or entirely be replaced with fluorine atom.

On the other hand, besides a base resin containing a repeating unit represented by the above-mentioned formula (10), there is also preferably used a base resin containing a repeating unit represented by the following formula (9).

[Chemical Formula 30]

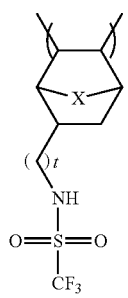

(9)

In the above formula (9), X represents any of —CH$_2$—, —O—, and —S—. t represents an integer of 1-6.

As molecular weight of the base resin, a polymer compound having the above-mentioned repeating unit and a weight average molecular weight of 1,000-1,000,000 is preferable. In case that molecular weight is less than this, it is not sufficient in terms of mechanical strength and film forming property. In case that molecular weight is greater than this, it is not preferable in terms of solubility in solvent and formability. Furthermore, it is also possible to blend at least of the above polymers.

To make the resist composition into a chemically amplified positive type, there is used a base resin that is insoluble or poorly soluble in a developing solution (normally, an alkali developing solution) and becomes soluble in the developing solution by acid. Therefore, one having an acid-labile group that is cleavable by acid is used.

A base resin containing a repeating unit having an acid-labile group is a polymer compound prepared by mixing a polymerizable monomer having an acid-labile group with a polymerizable monomer that generates the above-mentioned repeating unit and then conducting copolymerization, or one in which a part of the base resin containing the above-mentioned repeating unit has been converted into an acid-labile group. Examples of the acid-labile group can be used without a particular limitation, as long as they are groups that leave by the effect of the above-mentioned photoacid generator. As specific examples are mentioned, it is possible to mention alkykoxycarbonyl group, acetal group, silyl group, acyl group, etc. The alkoxycarbonyl group can be exemplified by tert-butoxycarbonyl group, tert-amyloxycarbonyl group, methoxycarbonyl group, ethoxycarbonyl group, i-propoxycarbonyl group, etc. As the acetal group, it is possible to mention methoxymethyl group, ethoxyethyl group, butoxyethyl group, cyclohexyloxyethyl group, benzyloxyethyl group, phenethyloxyethyl group, ethoxypropyl group, benzyloxypropyl group, phenethyloxypropyl group, ethoxybutyl group, ethoxyisobutyl group, etc. It is also possible to use an acetal group in which a vinyl ether has been added to a hydroxy group. As the silyl group, it is possible to mention, for example, trimethylsilyl group, ethyldimethylsilyl group, methyldiethylsilyl group, triethylsilyl group, i-propyldimethylsilyl group, methyldi-1-propylsilyl group, tri-1-propylsilyl group, t-butyldimethylsilyl group, methyldi-t-butylsilyl group, tri-t-butylsilyl group, phenyldimethylsilyl group, methyldiphenylsilyl group, triphenylsilyl group, etc. As the acyl group, it is possible to mention acetyl group, propionyl group, butyryl group, heptanoyl group, hexanoyl group, valeryl group, pivaloyl group, isovaleryl group, lauryloyl group, myristoyl group, palmytoyl group, stearoyl group, oxalyl group, malonyl group, succinyl group, glutaryl group, adipoyl group, piperoyl group, suberoyl group, azelaoyl group, sebacoyl group, acryloyl group, propioloyl group, methacryloyl group, crotonoyl group, oleoyl group, maleoyl group, fumaroyl group, mesaconoyl group, campholoyl group, benzoyl group, phthaloyl group, isophthaloyl group, terephthaloyl group, naphthoyl group, toluoyl group, hydratoropoyl group, atoropoyl group, cinnamoyl group, furoyl group, thenoyl group, nicotinoyl group, isonicotinoyl group, etc. Furthermore, it is also possible to use those in which hydrogen atoms of these acid-labile groups have partially or entirely be replaced with fluorine atom.

[Solvent]

As an organic solvent to be added to the resist composition of the present invention, any will do as long as it is an organic solvent in which base resin, acid generator, other additives, etc. are soluble. As such organic solvent, it is possible to use ketones such as acetone, methyl ethyl ketone, cyclohexanone, methyl isoamyl ketone and 2-heptanone; polyhydric alcohols such as ethylene glycol, ethylene glycol monoacetate, diethylene glycol, diethylene glycol monoacetate, propylene glycol, propylene glycol monoacetate, dipropylene glycol, or monomethyl ether, monoethyl ether, monopropyl ether, monobutyl ether or monophenyl ether of dipropylene glycol monoacetate, and their derivatives; cyclic ethers such as dioxane; esters such as methyl lactate, ethyl lactate, methyl acetate, ethyl acetate, butyl acetate, methyl pyruvate, ethyl pyruvate, methyl methoxypropionate, and ethyl ethoxypropionate; aromatic solvents such as xylene and toluene; fluorine-series solvents such as freon, alternative freon, perfluoro compounds, and hexafluoroisopropyl alcohol; and terpene-based petroleum naphtha solvents and paraffinic solvents, which are high-boiling-point, weak solvents, for the purpose of increasing applicability. These may be used singly or in a mixture of at least two kinds.

Usage of the organic solvent is 200-1,000 parts by weight relative to 100 parts by weight of the base resin, and particularly 400-800 parts by weight is preferable.

[Pattern Forming Method]

The resist composition of the present invention can preferably be used for pattern forming by going through each step of the step of applying the resist composition onto a substrate, the step of exposing it with a high-energy ray of a wavelength of 300 nm or less through a photomask after heating treatment, and the step of developing it by using developing solution, after heating treatment according to need.

As usage of the resist composition of the present invention, it is possible to use a resist pattern forming process of a conventional photoresist technique. That is, firstly the resist composition is applied on a substrate such as silicon wafer by using a spinner or the like. A photosensitive layer is formed by drying. This is irradiated with a high-energy ray through a desired mask pattern by an exposure device or the like, followed by heating. Then, this is subjected to a developing treatment by using a developing solution, for example, an alkali aqueous solution such as 0.1-10 weight % tetramethylammonium hydroxide aqueous solution. It is possible by this forming method to obtain a pattern conforming to the mask pattern. Furthermore, according to desire, it is possible to contain additives that are miscible with the resist material, for example, various additives such as additional resins, quencher, plasticizer, stabilizer, coloring agent, surfactant, tackifier, leveling agent, defoaming agent, compatibility enhancing agent, adhesion enhancing agent, antioxidant, etc.

A high-energy ray of a wavelength of 300 nm or less used in the present invention is not particularly limited. In particular, in the case of conducting a fine processing, it is effective to use an exposure device equipped with a source for generating a short-wavelength high-energy ray such as ArF excimer laser, KrF excimer laser, or soft X-ray. It is effective to use an immersion exposure device that makes it possible to conduct a more efficient fine processing in numerical aperture and effective wavelength by using a medium, such as water or a fluorine-based solvent, into which the high-energy ray to be used has a less absorption, at a part of the optical path. The present resist material is preferable in the case of use in this device.

Of the above-mentioned pattern forming methods, an immersion lithography, in which an ArF excimer laser of 193 nm in wavelength is used and in which water is inserted between wafer and projector lens, is one of particularly preferable modes.

The present invention is explained in more detail by giving examples in the following, but the present invention is not limited by these.

EXAMPLES

Synthesis Example 1

Production of (2-bromo-2,2-difluoro)ethyl valerate

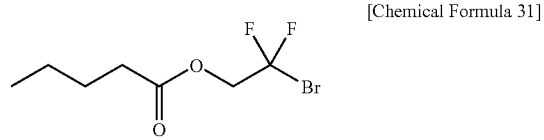

[Chemical Formula 31]

A 200 mL reactor was charged under nitrogen with 6.0 g (50.0 millimoles) of valeryl chloride and 90 mL of THF (dehydrated), followed by putting it in an iced bath. There 11.3 g (purity: 93%, 65.3 millimoles/1.31 equivalents) of 2-bromo-2,2-difluoroethanol was added, and 7.1 g (70.0 millimoles/1.4 equivalents) of triethylamine was added dropwise. After the dropping, stirring was conducted at room temperature for 18 hours. Then, 35 mL of water was added, and extraction was conducted two times with 100 mL of diisopropyl ether. The obtained organic layer was further washed with diluted hydrochloric acid, sodium bicarbonate water and brine, followed by removing water with sodium sulfate, filtration, and then distilling isopropyl ether off, thereby obtaining 9.9 g of the target (2-bromo-2,2-difluoro)ethyl valerate. Upon this, purity was 89%, and yield was 72%.

Properties of (2-bromo-2,2-difluoro)ethyl valerate $^1$H NMR (CDCl$_3$): d 4.53 (t, J=11.6 Hz, 2H; CH$_2$), 2.36 (t, J=7.6 Hz, 2H; CH$_2$), 1.59 (quintet, J=7.6 Hz, 2H; CH$_2$), 1.31 (sextet, J=7.6 Hz, 2H; CH$_2$), 0.86 (t, J=7.6 Hz, 3H; CH$_3$).
$^{19}$F NMR (CDCl$_3$) d -56.74 (t, J=11.6 Hz, 2F; CF$_2$).

Synthesis Example 2

Production of sodium 2-valeryloxy-1,1-difluoroethanesulfinate

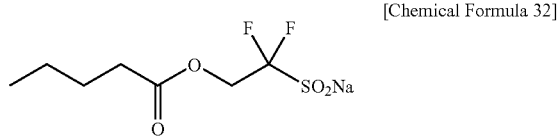

[Chemical Formula 32]

A 200 mL container was charged under nitrogen with 9.7 g (purity 89%, 35.4 millimoles) of (2-bromo-2,2-difluoro)ethyl valerate, 40 g of acetonitrile, 5.9 g (70.7 millimoles/2.0 equivalents) of sodium hydrogencarbonate, 8.7 g (50.1 millimoles/1.5 equivalents) of sodium dithionite, and 40 g of water, and stirring was conducted at 60 degrees for 1.5 hours and at 80 degrees for 16 hours. Furthermore, 5.9 g (70.7 millimoles) of sodium hydrogencarbonate and 8.7 g (50.1 millimoles) of sodium dithionate were added, and stirring was conducted at 80 degrees for 94 hours. The reaction liquid was extracted six times with 40 mL of acetonitrile, and the solvent was distilled out of the obtained organic layer. Furthermore, it was washed with 200 mL of diisopropyl ether, followed by filtration and drying solid, thereby obtaining 6.74 g of the target sodium 2-valeryloxy-1,1-difluoroethanesulfinate. Upon this, purity was 28%, and yield was 21%.

Properties of sodium
2-valeryloxy-1,1-difluoroethanesulfinate $^1$H NMR (CDCl$_3$): d 4.42 (t, J=16.4 Hz, 2H; CH$_2$), 2.34 (t, J=7.6 Hz, 2H; CH$_2$), 1.50 (quintet, J=7.6 Hz, 2H; CH$_2$), 1.28 (sextet, J=7.6 Hz, 2H; CH$_2$), 0.85 (t, J=7.6 Hz, 3H; CH$_3$).
$^{19}$F NMR (CDCl$_3$) d -119.95 (t, J=16.4 Hz, 2F; CF$_2$).

Synthesis Example 3

Production of sodium
2-valeryloxy-1,1-difluoroethanesulfonate

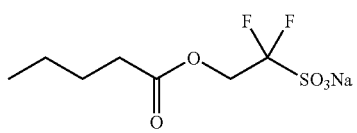

[Chemical Formula 33]

A 100 mL reactor was charged with 6.6 g (purity 28%, 7.3 millimoles) of sodium 2-valeryloxy-1,1-difluoroethanesulfinate, 60 mL of water, 0.0047 g (0.014 millimoles/0.0019 equivalents) of sodium tungstate dihydrate, and 1.9 g (16.4 millimoles/2.25 equivalents) of 30% hydrogen peroxide solution, followed by stirring at room temperature for 1.5 hours. The reaction liquid was heated under reduced pressure, followed by distilling volatile component to dryness, thereby obtaining 6.6 g of the target sodium 2-valeryloxy-1,1-difluoroethanesulfonate. Upon this, purity was 26%, and yield was 88%.

Properties of sodium
2-valeryloxy-1,1-difluoroethanesulfonate $^1$H NMR (DMSO-d$_6$): δ 4.52 (t, J=15.6 Hz, 2H; CH$_2$), 2.34 (t, J=7.6 Hz, 2H; CH$_2$), 1.51 (quintet, J=7.6 Hz, 2H; CH$_2$), 1.28 (sextet, J=7.6 Hz, 2H; CH$_2$), 0.85 (t, J=7.6 Hz, 3H; CH$_3$).
$^{19}$F NMR (DMSO-d$_6$) d -113.70 (t, J=15.6 Hz, 2F; CF$_2$).

Synthesis Example 4

Production of triphenylsulfonium
2-valeryloxy-1,1-difluoroethanesulfonate

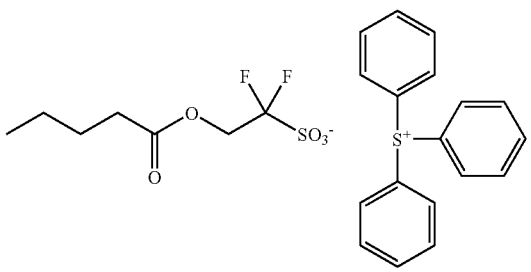

[Chemical Formula 34]

A 100 mL reactor was charged with 3.0 g (purity 26%, 2.9 millimoles) of sodium 2-valeryloxy-1,1-difluoroethanesulfonate and 30 g of water, followed by adding dropwise an aqueous solution of triphenylsulfonium chloride [17.8 g (5.2 millimoles/1.8 equivalents) of triphenylsulfonium chloride and 16.2 g of water] at room temperature, followed by stirring at room temperature for 1.5 hours. Then, extraction was conducted by adding 30 mL of chloroform. The obtained organic layer was washed two times with water, followed by distilling solvent off, thereby obtaining 0.96 g of the target triphenylsulfonium 2-valeryloxy-1,1-difluoroethanesulfonate. Upon this, purity was 98%, and yield was 64%.

Properties of triphenylsulfonium
2-valeryloxy-1,1-difluoroethanesulfonate $^1$H NMR (DMSO-d$_6$): δ 7.92-7.70 (15H; Ph$_3$S$^+$), 4.52 (t, J=15.6 Hz, 2H; CH$_2$), 2.36 (t, J=7.2 Hz, 2H; CH$_2$), 1.49 (quintet, J=7.2 Hz, 2H; CH$_2$), 1.28 (sextet, J=7.2 Hz, 2H; CH$_2$), 0.85 (t, J=7.2 Hz, 3H; CH$_3$).
$^{19}$F NMR (DMSO-d$_6$) d -113.72 (t, J=15.6 Hz, 2F; CF$_2$).

Synthesis Example 5

Production of (2'-bromo-2',2'-difluoro)ethyl
1-adamantanecarboxylate

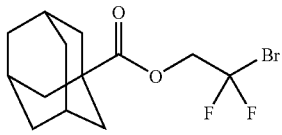

[Chemical Formula 35]

A 300 mL reactor was charged under nitrogen with 14.2 g (71.3 millimoles) of 1-adamantanecarbonyl chloride and 120 mL of THF (dehydrated), followed by putting it in an iced bath. There 16.1 g (purity: 92%, 91.8 millimoles/1.29 equivalents) of 2-bromo-2,2-difluoroethanol was added, and 10.1 g (99.8 millimoles/1.4 equivalents) of triethylamine was added dropwise. After the dropping, stirring was conducted at 60 degrees for 23 hours. Then, 50 mL of water was added, and extraction was conducted two times with 150 mL of diisopropyl ether. The obtained organic layer was further washed with diluted hydrochloric acid, sodium bicarbonate water and brine, followed by removing water with sodium sulfate, filtration, and then distilling isopropyl ether off, thereby obtaining 23.2 g of the target (2'-bromo-2',2'-difluoro)ethyl 1-adamantanecarboxylate. Upon this, purity was 85%, and yield was 86%.

Properties of (2'-bromo-2',2'-difluoro)ethyl
1-adamantanecarboxylate $^1$H NMR (CDCl$_3$): d 4.51 (t, J=11.6 Hz, 2H; CH$_2$), 1.97 (m, 3H; 1-Ad), 1.87 (m, 6H; 1-Ad), 1.66 (m, 6H; 1-Ad).
$^{19}$F NMR (CDCl$_3$) d -56.46 (t, J=11.6 Hz, 2F; CF$_2$).

Synthesis Example 6

Production of sodium 2-(1'-adamantane)carbonyloxy-1,1-difluoroethanesulfinate

[Chemical Formula 36]

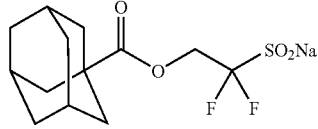

A 300 mL container was charged under nitrogen with 22.8 g (purity 85%, 60.0 millimoles) of (2'-bromo-2',2'-difluoro)ethyl 1-adamantanecarboxylate, 80 g of acetonitrile, 10.1 g (120.0 millimoles/2.0 equivalents) of sodium hydrogencarbonate, 15.7 g (90.0 millimoles/1.5 equivalents) of sodium dithionite, and 80 g of water, and stirring was conducted at 70 degrees for 66 hours. Furthermore, 6.7 g (80.0 millimoles) of sodium hydrogencarbonate and 10.5 g (60.0 millimoles) of sodium dithionate were added, and stirring was conducted at 80 degrees for 24 hours. The reaction liquid was extracted one time with 30 mL of acetonitrile, and the solvent was distilled out of the obtained organic layer. Furthermore, it was washed with 400 mL of diisopropyl ether, followed by filtration and drying solid, thereby obtaining 12.0 g of the target sodium 2-(1'-adamantane)carbonyloxy-1,1-difluoroethanesulfinate. Upon this, purity was 65%. Furthermore, the solvent was distilled out of the washing liquid, thereby recovering 11.3 g of (2'-bromo-2',2'-difluoro)ethyl 1-adamantanecarboxylate. Upon this, purity was 71%.

A 200 mL container was charged under nitrogen with 11.1 g (purity 71%, 24.4 millimoles) of recovered (2'-bromo-2',2'-difluoro)ethyl 1-adamantanecarboxylate, 40 g of acetonitrile, 4.1 g (48.8 millimoles/2.0 equivalents) of sodium hydrogencarbonate, 6.4 g (36.6 millimoles/1.5 equivalents) of sodium dithionite, and 40 g of water, and stirring was conducted at 80 degrees for 18 hours. Furthermore, 1.9 g (22.4 millimoles) of sodium hydrogencarbonate and 2.9 g (16.8 millimoles) of sodium dithionate were added, and stirring was conducted at 80 degrees for 22 hours. The reaction liquid was extracted one time with 30 mL of acetonitrile, and the solvent was distilled out of the obtained organic layer. Furthermore, it was washed with 250 mL of diisopropyl ether, followed by filtration and drying solid, thereby obtaining 6.9 g of the target sodium 2-(1'-adamantane)carbonyloxy-1,1-difluoroethanesulfinate. Upon this, purity was 61%.

Properties of sodium 2-(1'-adamantane)carbonyloxy-1,1-difluoroethanesulfinate $^1$H NMR (DMSO-$d_6$): δ 4.42 (t, J=16.4 Hz, 2H; $CH_2$), 1.93 (m, 3H; 1-Ad), 1.80 (m, 6H; 1-Ad), 1.63 (m, 6H; 1-Ad).
$^{19}$F NMR (DMSO-$d_6$) d -120.23 (t, J=16.4 Hz, 2F; $CF_2$).

Synthesis Example 7

Production of sodium 2-(1'-adamantane)carbonyloxy-1,1-difluoroethanesulfonate

[Chemical Formula 37]

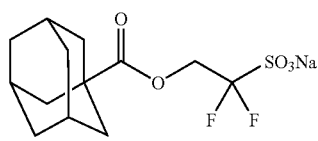

A 300 mL reactor was charged with 18.6 g (purity 64%, 36.0 millimoles) of sodium 2-(1'-adamantane)carbonyloxy-1,1-difluoroethanesulfinate, 120 mL of water, 0.0154 g (0.047 millimoles/0.0013 equivalents) of sodium tungstate dihydrate, and 6.1 g (53.9 millimoles/1.5 equivalents) of 30% hydrogen peroxide solution, followed by stirring at room temperature for 2 hours. The reaction liquid was heated under reduced pressure, followed by distilling volatile component to dryness, thereby obtaining 18.6 g of the target sodium 2-(1'-adamantane)carbonyloxy-1,1-difluoroethanesulfonate. Upon this, purity was 65%, and yield was 97%.

Properties of sodium 2-(1'-adamantane)carbonyloxy-1,1-difluoroethanesulfonate $^1$H NMR (DMSO-$d_6$): δ 4.51 (t, J=15.3 Hz, 2H; $CH_2$), 1.96 (m, 3H; 1-Ad), 1.82 (m, 6H; 1-Ad), 1.65 (m, 6H; 1-Ad).
$^{19}$F NMR (DMSO-$d_6$) d -113.94 (t, J=15.3 Hz, 2F; $CF_2$).

Synthesis Example 8

Production of triphenylsulfonium 2-(1'-adamantane)carbonyloxy-1,1-difluoroethanesulfonate

[Chemical Formula 38]

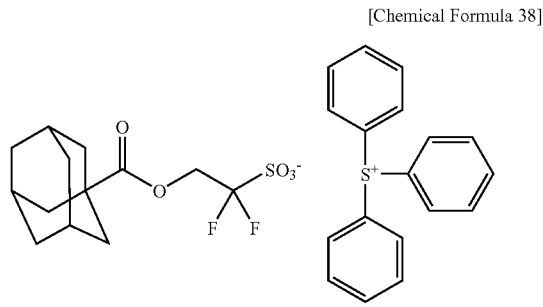

A 200 mL reactor was charged with 9.5 g (purity 65%, 17.8 millimoles) of sodium 2-(1'-adamantane)carbonyloxy-1,1-difluoroethanesulfonate and 85 g of water, followed by adding dropwise an aqueous solution of triphenylsulfonium chloride [5.6 g (19.6 millimoles/1.1 equivalents) of triphenylsulfonium chloride and 61.7 g of water] at room temperature. Then, stirring was conducted at room temperature for 1.5 hours, followed by filtration and drying solid, thereby obtaining 9.8 g of the target triphenylsulfonium 2-(1'-adamantane)carbonyloxy-1,1-difluoroethanesulfonate. Upon this, purity was 98%, and yield was 92%.

Properties of triphenylsulfonium 2-(1'-adamantane)carbonyloxy-1,1-difluoroethanesulfonate $^1$H NMR (DMSO-$d_6$): δ 7.91-7.72 (15H; $Ph_3S^+$), 4.51 (t, J=15.3 Hz, 2H; $CH_2$), 1.96 (m, 3H; 1-Ad), 1.82 (m, 6H; 1-Ad), 1.65 (m, 6H; 1-Ad).
$^{19}$F NMR (DMSO-$d_6$) d -113.97 (t, J=15.3 Hz, 2F; $CF_2$).

Synthesis Example 9

Production of (2'-bromo-2',2'-difluoro)ethyl 3-hydroxy-1-adamantanecarboxylate

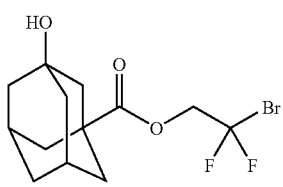

[Chemical Formula 39]

A 300 mL reactor was charged under nitrogen with 23.3 g (108.6 millimoles) of 3-hydroxy-1-adamantanecarbonyl chloride and 200 mL of THF (dehydrated), followed by putting it in an iced bath. There 20.0 g (124 millimoles/1.15 equivalents) of 2-bromo-2,2-difluoroethanol was added, and 16.5 g (163 millimoles/1.5 equivalents) of triethylamine was added dropwise. After the dropping, stirring was conducted at room temperature for 1 hour. Then, 100 mL of water was added, and extraction was conducted two times with 150 mL of diisopropyl ether. The obtained organic layer was further washed with diluted hydrochloric acid, sodium bicarbonate water and brine, followed by removing water with sodium sulfate, filtration, and then distilling diisopropyl ether off, thereby obtaining 34.7 g of the target (2'-bromo-2',2'-difluoro)ethyl 3-hydroxy-1-adamantanecarboxylate. Upon this, purity was 99%, and yield was 94%.

Properties of (2'-bromo-2',2'-difluoro)ethyl 3-hydroxy-1-adamantanecarboxylate $^{19}$F NMR (DMSO-$d_6$) d -55.44 (t, J=12 Hz, 2F; $CF_2$).

Synthesis Example 10

Production of sodium 2-(3'-hydroxy-1'-adamantane)carbonyloxy-1,1-difluoroethanesulfonate

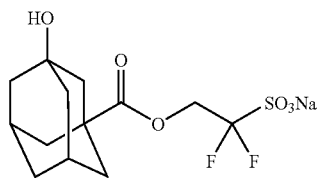

[Chemical Formula 40]

A 500 mL container was charged under nitrogen with 32.95 g (purity 99%, 97.0 millimoles) of (2'-bromo-2',2'-difluoro)ethyl 3-hydroxy-1-adamantanecarboxylate, 90 g of acetonitrile, 11 g (131 millimoles/1.35 equivalents) of sodium hydrogencarbonate, 25 g (144 millimoles/1.48 equivalents) of sodium dithionite, and 70 g of water, and stirring was conducted at 65 degrees for 16 hours. Stirring was stopped to have the two layers separated, followed by removing the aqueous layer. To the remaining organic layer, 11 g (131 millimoles/1.35 equivalents) of sodium hydrogencarbonate, 25 g (144 millimoles/1.48 equivalents) of sodium dithionite, and 70 g of water were added, followed by stirring at 65 degrees for 5 hours. This operation was further repeated two times (that is, an aqueous solution of sodium hydrogencarbonate and sodium dithionite was used four times). Stirring was stopped to have the two layers separated. The aqueous layer was extracted one time with 30 mL of acetonitrile. The obtained organic layers were combined together, and the solvent was distilled off. Furthermore, it was washed with 400 mL of diisopropyl ether, followed by filtration and drying solid, thereby obtaining sodium 2-(3'-hydroxy-1'-adamantane)carbonyloxy-1,1-difluoroethanesulfinate.

To the obtained sodium 2-(3'-hydroxy-1'-adamantane)carbonyloxy-1,1-difluoroethanesulfinate, 120 mL of water and 19 g of 30% hydrogen peroxide solution were added, followed by stirring at room temperature for 16 hours. The reaction liquid was heated under reduced pressure to distill volatile component off to dryness, thereby obtaining 20.0 g of the target sodium 2-(3'-hydroxy-1'-adamantane)carbonyloxy-1,1-difluoroethanesulfonate. Upon this, purity was 68%, and yield was 57%.

Properties of sodium 2-(3'-hydroxy-1'-adamantane)carbonyloxy-1,1-difluoroethanesulfonate $^1$H NMR (DMSO-$d_6$): δ 10.1 (br, 1H; OH), 4.54 (t, J=15.6 Hz, 2H; $CH_2$), 2.6-1.3 (14H).
$^{19}$F NMR (DMSO-$d_6$) d -108.57 (t, J=15.6 Hz, 2F; $CF_2$).

Synthesis Example 11

Production of triphenylsulfonium 2-(3'-hydroxy-1'-adamantane)carbonyloxy-1,1-difluoroethanesulfonate

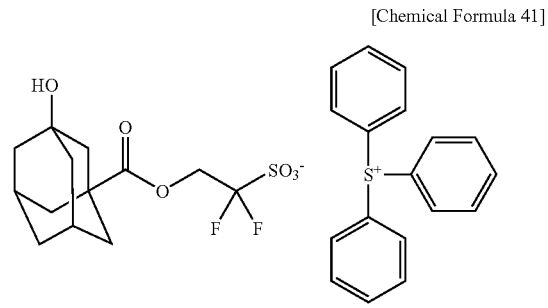

[Chemical Formula 41]

A 200 mL reactor was charged with 30.9 g (purity 68%, 58.1 millimoles) of sodium 2-(3'-hydroxy-1'-adamantane)carbonyloxy-1,1-difluoroethanesulfonate and 150 g of water, followed by adding dropwise at room temperature a chloroform (150 ml) solution of triphenylsulfonium bromide of 23.5 g (68.5 millimoles/1.18 equivalents). Then, stirring was conducted at room temperature for two hours, followed by having the two layers separated to recover the organic layer. The obtained organic layer was washed four times with 150 ml of water. Then, the solvent was distilled out of the organic layer, thereby obtaining 35.0 g of the target triphenylsulfonium 2-(3'-hydroxy-1'-adamantane)carbonyloxy-1,1-difluoroethanesulfonate. Upon this, purity was 97%, and yield was 99%.

Properties of triphenylsulfonium 2-(3'-hydroxy-1'-adamantane)carbonyloxy-1,1-difluoroethanesulfonate $^1$H NMR (DMSO-$d_6$): δ 7.8-7.6 (15H; $Ph_3S^+$), 4.69 (t, J=16 Hz, 2H; $CH_2$), 2.2-1.7 (12H), 1.55 (s, 2H).
$^{19}$F NMR (DMSO-$d_6$) d −114.59 (t, J=16 Hz, 2F; $CF_2$).

Test Example 1

Photo Acid Generation Function of triphenylsulfonium 2-(1'-adamantane)carbonyloxy-1,1-difluoroethanesulfonate An acetonitrile solution of sodium 2-(1'-adamantane)carbonyloxy-1,1-difluoroethanesulfonate synthesized in Synthesis Example 8 was prepared to have a concentration of 0.05 mol/L. It was put into a quartz optical cell having an optical path length of 1 cm, followed by irradiation with a light (290 nm) separated from a xenon lamp to conduct actinometry of acid generation. The amount of acid generated was observed by absorption of tetrabromophenol blue at 610 nm. Quantity of light was measured with potassium iron trioxalate to determine quantum yield. With this, it was 0.21 showing a high acid generation function.

Test Example 2

Photo Acid Generation Function of triphenylsulfonium 2-(3'-hydroxy-1'-adamantane)carbonyloxy-1,1-difluoroethanesulfonate An acetonitrile solution of sodium 2-(3'-hydroxy-1'-adamantane)carbonyloxy-1,1-difluoroethanesulfonate synthesized in Synthesis Example 11 was prepared to have a concentration of 0.05 mol/L. It was put into a quartz optical cell having an optical path length of 1 cm, followed by irradiation with a light (290 nm) separated from a xenon lamp to conduct actinometry of acid generation. The amount of acid generated was observed by absorption of tetrabromophenol blue at 610 nm. Quantity of light was measured with potassium iron trioxalate to determine quantum yield. With this, it was 0.20 showing a high acid generation function.

Test Example 3

Solubility of triphenylsulfonium 2-(1'-adamantane)carbonyloxy-1,1-difluoroethanesulfonate 1.0 g of sodium 2-(1'-adamantane)carbonyloxy-1,1-difluoroethanesulfonate synthesized in Synthesis Example 8 was weighed and added to 100 g of propylene glycol methyl ether acetate, followed by stirring. With this, it was completely dissolved.

Test Example 4

Solubility of triphenylsulfonium 2-(3'-hydroxy-1'-adamantane)carbonyloxy-1,1-difluoroethanesulfonate 1.0 g of sodium 2-(3'-hydroxy-1'-adamantane)carbonyloxy-1,1-difluoroethanesulfonate synthesized in Synthesis Example 11 was weighed and added to 10 g of propylene glycol methyl ether acetate, followed by stirring. With this, it was completely dissolved.

Application Example 1

A resist was prepared by dissolving 2 parts by weight of triphenylsulfonium 2-valeryloxy-1,1-difluoroethanesulfonate mentioned in Synthesis Example 4, 100 parts by weight of a polymer having a weight average molecular weight of 15,000, in which hydroxy groups of polyhydroxystyrene have been protected with 15 mol % of 1-ethoxyethyl group and 15 mol % of tert-butoxycarbonyl group, and 0.2 parts by weight of isopropanolamine in 600 parts by weight of propylene glycol monomethyl ether acetate.

Application Example 2

A resist was prepared by dissolving 2 parts by weight of triphenylsulfonium 2-(1'-adamantane)carbonyloxy-1,1-difluoroethanesulfonate mentioned in Synthesis Example 8, 100 parts by weight of a polymer having a weight average molecular weight of 15,000, in which hydroxy groups of polyhydroxystyrene have been protected with 35 mol % of 1-ethoxyethyl group, and 0.2 parts by weight of isopropanolamine in 600 parts by weight of propylene glycol monomethyl ether acetate.

Application Example 3

A resist was prepared by dissolving 5 parts by weight of triphenylsulfonium 2-(1'-adamantane)carbonyloxy-1,1-difluoroethanesulfonate mentioned in Synthesis Example 8, 100 parts by weight of a terpolymer (weight average molecular weight 12800) of 45 mol % methyladamantanemethacrylate/25 mol % hydroxyadamantanemethacrylate/30 mol γ-bulyrolactonemethacrylate, 0.1 parts by weight of triethanolamine in 800 parts by weight of propylene glycol monomethyl ether acetate.

Application Example 4

A resist was prepared by dissolving 2 parts by weight of triphenylsulfonium 2-(3'-hydroxy-1'-adamantane)carbonyloxy-1,1-difluoroethanesulfonate mentioned in Synthesis Example 11, 100 parts by weight of a polymer having a weight average molecular weight of 15,000, in which hydroxy groups of polyhydroxystyrene have been protected with 35 mol % of 1-ethoxyethyl group, and 0.2 parts by weight of isopropanolamine in 600 parts by weight of propylene glycol monomethyl ether acetate.

Test Example 5

The resists of Application Examples 1, 2, 3 and 4 were filtered by a membrane filter of 0.2 µm to prepare radiosensitive resin composition solutions. Then, the composition solutions were applied on silicon wafers with a rotation speed of 1500 rpm. Then, they were dried at 100° C. for 90 seconds on a hot plate to form resist films having a film thickness of 320 nm. The obtained films were homogeneous and good.

This resist film was subjected to exposure by using an ultraviolet ray by a high-pressure mercury light. After exposure, heating was conducted on the hot plate at 110° C. for 90 seconds. An immersion phenomenon was conducted for 60 seconds in 2.38% tetramethylammonium hydroxide aqueous solution, and rinse was conducted for 30 seconds with pure water.

As a result, in all of Application Examples 1, 2, 3 and 4 there were obtained rectangular, positive-type, good patterns having less edge roughness.

Regarding sulfonium salts (PAG 1, 2 and 5) represented by the following formulas, there were conducted evaluations of compatibility and resolution when resists were formed.

[Chemical Formula 42]

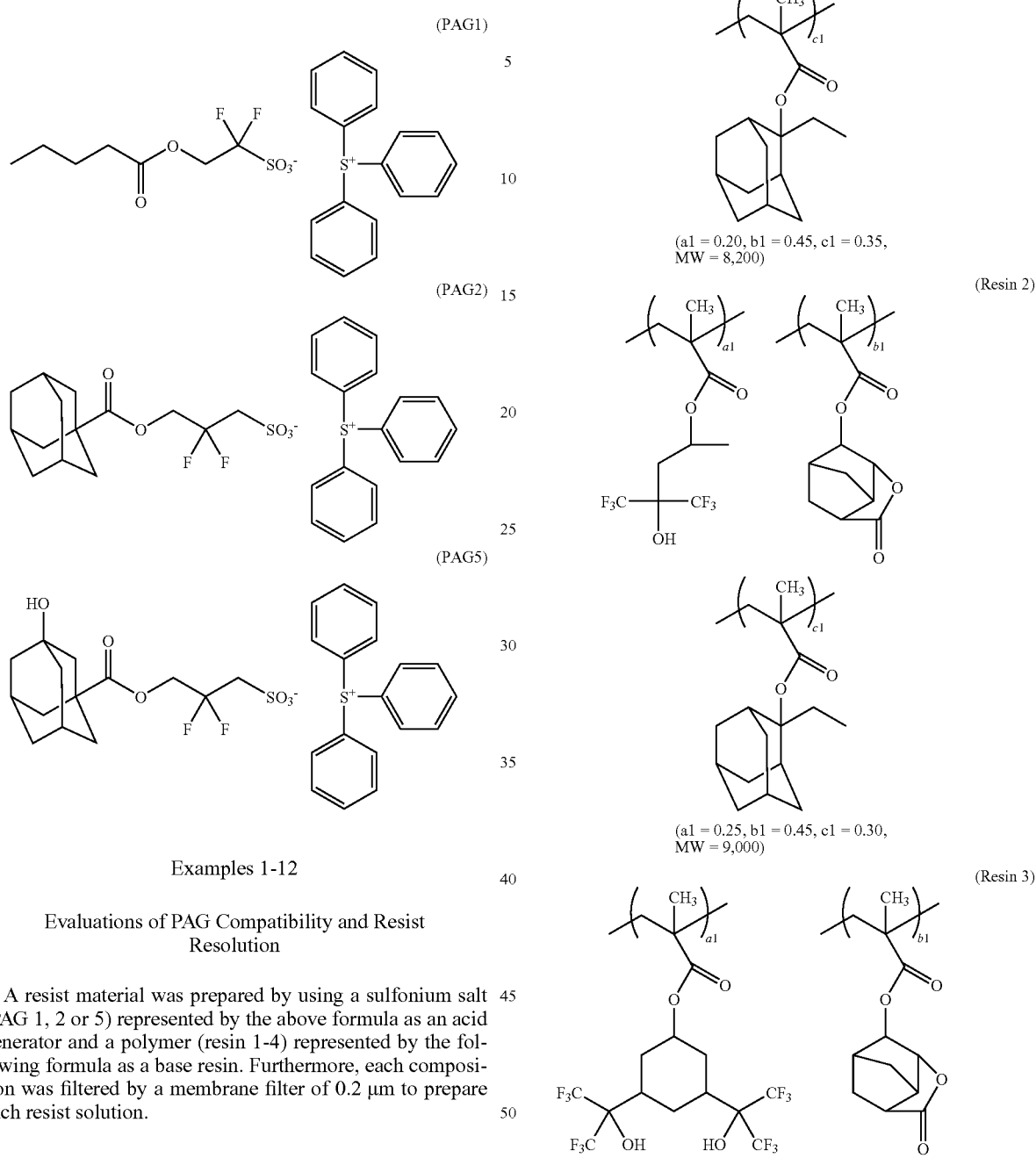

Examples 1-12

Evaluations of PAG Compatibility and Resist Resolution

A resist material was prepared by using a sulfonium salt (PAG 1, 2 or 5) represented by the above formula as an acid generator and a polymer (resin 1-4) represented by the following formula as a base resin. Furthermore, each composition was filtered by a membrane filter of 0.2 μm to prepare each resist solution.

[Chemical Formula 43]

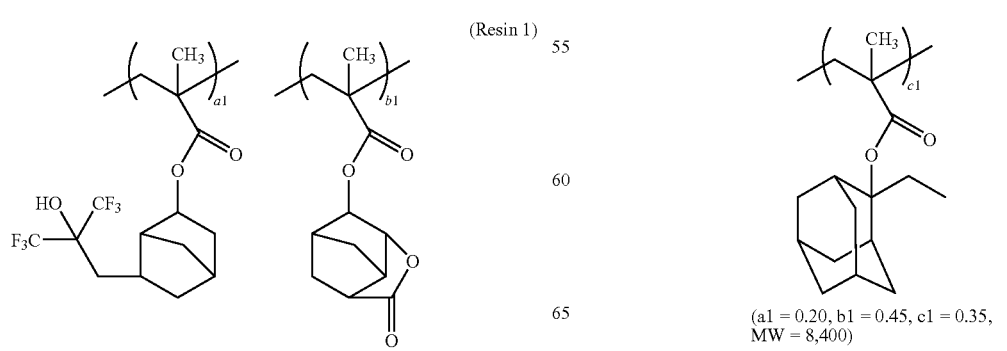

-continued

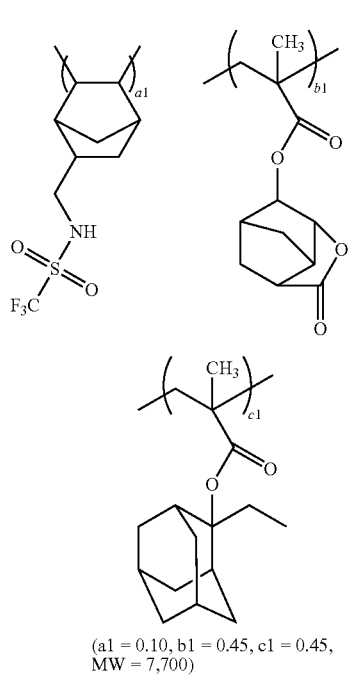

(Resin 4)

(a1 = 0.10, b1 = 0.45, c1 = 0.45, MW = 7,700)

Then, all of the resist solutions were applied on silicon wafers by spin coating to obtain resist films having a film thickness of 250 nm. After conducting a prebaking at 110° C., exposure was conducted with 248 nm ultraviolet ray through a photomask, and then a post-exposure baking was conducted at 120° C. After that, development was conducted at 23° C. for 1 minute by using 2.38 wt % tetramethylammonium hydroxide aqueous solution. Composition and evaluation results of each resist are shown in Table 1.

Comparative Examples

For comparison, with respect to sulfonium salts (PAG 3 and 4) represented by the following formulas, evaluations of compatibility of PAG when made into resists and resolution of resists are shown in Table 2.

[Chemical Formula 44]

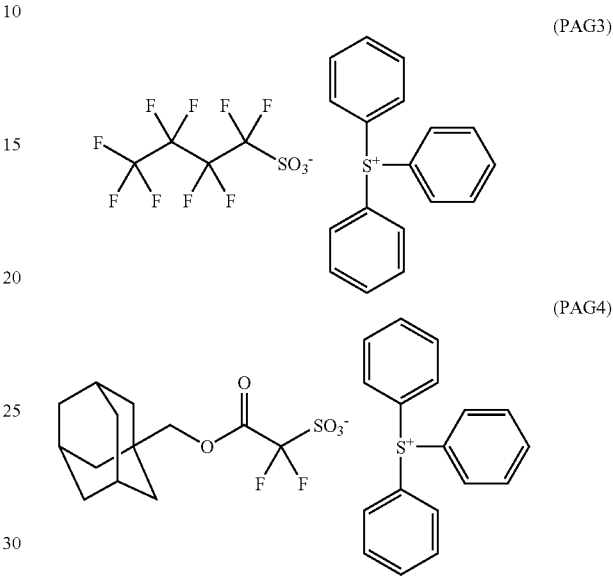

Comparative Examples 1-8

Evaluations of Compatibility of PAG and Resolution of Resists

TABLE 1

| Example | Resin (parts by wt.) | Acid Generator (parts by wt.) | Solvent (parts by wt.) | Compat-ibility | Pattern Shape |
|---|---|---|---|---|---|
| 1 | Resin 1 (40) | PAG 1 (1.0) | PGMEA (400) | Good | Clean rectangular |
| 2 | Resin 1 (40) | PAG 2 (1.0) | PGMEA (400) | Good | Clean rectangular |
| 3 | Resin 1 (40) | PAG 5 (1.0) | PGMEA (400) | Good | Clean rectangular |
| 4 | Resin 2 (40) | PAG 1 (1.0) | PGMEA (400) | Good | Clean rectangular |
| 5 | Resin 2 (40) | PAG 2 (1.0) | PGMEA (400) | Good | Clean rectangular |
| 6 | Resin 2 (40) | PAG 5 (1.0) | PGMEA (400) | Good | Clean rectangular |
| 7 | Resin 3 (40) | PAG 1 (1.0) | PGMEA (400) | Good | Clean rectangular |
| 8 | Resin 3 (40) | PAG 2 (1.0) | PGMEA (400) | Good | Clean rectangular |
| 9 | Resin 3 (40) | PAG 5 (1.0) | PGMEA (400) | Good | Clean rectangular |
| 10 | Resin 4 (40) | PAG 1 (1.0) | PGMEA (400) | Good | Clean rectangular |
| 11 | Resin 4 (40) | PAG 2 (1.0) | PGMEA (400) | Good | Clean rectangular |
| 12 | Resin 4 (40) | PAG 5 (1.0) | PGMEA (400) | Good | Clean rectangular |

TABLE 2

| Comparative Example | Resin (parts by wt.) | Acid Generator (parts by wt.) | Solvent (parts by wt.) | Compat-ibility | Pattern Shape |
|---|---|---|---|---|---|
| 1 | Resin 1 (40) | PAG 3 (1.0) | PGMEA (400) | Good | Somewhat head-swollen shape |
| 2 | Resin 1 (40) | PAG 4 (1.0) | PGMEA (400) | Good | Somewhat distorted rectangular |
| 3 | Resin 2 (40) | PAG 3 (1.0) | PGMEA (400) | Somewhat defective | Somewhat head-swollen shape |
| 4 | Resin 2 (40) | PAG 4 (1.0) | PGMEA (400) | Good | Clean rectangular (*) |
| 5 | Resin 3 (40) | PAG 3 (1.0) | PGMEA (400) | Somewhat defective | Somewhat head-swollen shape |
| 6 | Resin 3 (40) | PAG 4 (1.0) | PGMEA (400) | Good | Clean rectangular (*) |
| 7 | Resin 4 (40) | PAG 3 (1.0) | PGMEA (400) | Somewhat defective | Somewhat head-swollen shape |
| 8 | Resin 4 (40) | PAG 4 (1.0) | PGMEA (400) | Good | Somewhat distorted rectangular |

(*) somewhat inferior to Examples.

From the results of Table 1 and Table 2, it was confirmed that the resist compositions of the present invention had resolutions higher than those of conventional products.

The invention claimed is:

1. A fluorine-containing N-sulfonyloxyimide compound represented by the following formula (6)

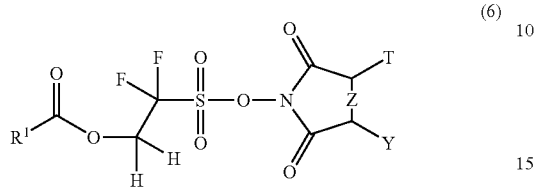

(6)

wherein $R^1$ represents
a $C_{1-10}$ straight-chain or branched alkyl group, wherein hydrogen atoms of the alkyl group may partially or entirely be replaced with fluorine or hydroxyl group, and two hydrogen atoms on the same carbon constituting the alkyl group may be replaced with a single oxygen atom to make a keto group,
a $C_{1-10}$ straight-chain or branched alkenyl group having a double bond at an end portion at least, wherein hydrogen atoms of the end alkenyl group may partially or entirely be replaced with fluorine or hydroxyl group, and two hydrogen atoms on the same carbon constituting the end alkenyl group may be replaced with a single oxygen atom to make a keto group,
a $C_{3-20}$ alicyclic organic group, wherein hydrogen atoms of the alicyclic organic group may partially or entirely be replaced with fluorine or hydroxyl group, and two hydrogen atoms on the same carbon constituting the alicyclic organic group may be replaced with a single oxygen atom to make a keto group,
a $C_{6-20}$ aryl group, a $C_{1-10}$ straight-chain or branched alkoxyl group, wherein hydrogen atoms of the alkoxyl group may partially or entirely be replaced with fluorine or hydroxyl group,
a $C_{6-20}$ aryloxy group, wherein hydrogen atoms of the aryloxy group may partially or entirely be replaced with fluorine or hydroxyl group,
a $C_{2-10}$ straight-chain or branched alkylcarbonyl group, wherein hydrogen atoms of the alkylcarbonyl group may partially or entirely be replaced with fluorine or hydroxyl group,
a $C_{7-20}$ arylcarbonyl group, wherein hydrogen atoms of the arylcarbonyl group may partially or entirely be replaced with fluorine or hydroxyl group,
a $C_{2-10}$ straight-chain or branched alkylcarbonyloxy group, wherein hydrogen atoms of the alkylcarbonyloxy group may partially or entirely be replaced with fluorine or hydroxyl group,
a $C_{7-20}$ arylcarbonyloxy group, wherein hydrogen atoms of the arylcarbonyloxy group may partially or entirely be replaced with fluorine or hydroxyl group,
a $C_{1-10}$ straight-chain or branched alkoxycarbonyl group, wherein hydrogen atoms of the alkoxycarbonyl group may partially or entirely be replaced with fluorine or hydroxyl group, or
a $C_{7-20}$ aryloxycarbonyl group, wherein hydrogen atoms of the aryloxycarbonyl group may partially or entirely be replaced with fluorine or hydroxyl group b,
wherein Z represents a single bond, double bond, methylene group or oxygen atom, and wherein T and Y independently represent hydrogen atoms or $C_{1-10}$ substituted or unsubstituted alkyl groups, or T and Y jointly may form an alicyclic structure, aromatic ring structure or hetero ring structure by including carbon atoms to which they are attached.

2. A photoacid generator containing a fluorine-containing N-sulfonyloxyimide compound according to claim 1.

3. A fluorine-containing oximesulfonate compound represented by the following formula (7),

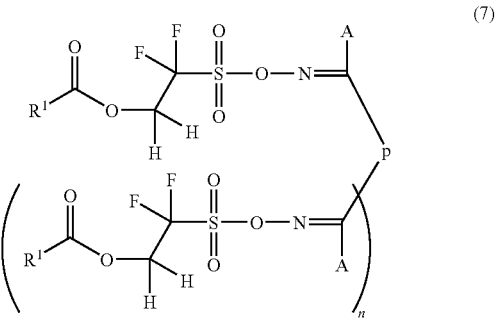

(7)

wherein $R^1$ represents
a $C_{1-10}$ straight-chain or branched alkyl group, wherein hydrogen atoms of the alkyl group may partially or entirely be replaced with fluorine or hydroxyl group, and two hydrogen atoms on the same carbon constituting the alkyl group may be replaced with a single oxygen atom to make a keto group,
a $C_{1-10}$ straight-chain or branched alkenyl group having a double bond at an end portion at least, wherein hydrogen atoms of the end alkenyl group may partially or entirely be replaced with fluorine or hydroxyl group, and two hydrogen atoms on the same carbon constituting the end alkenyl group may be replaced with a single oxygen atom to make a keto group,
a $C_{3-20}$ alicyclic organic group, wherein hydrogen atoms of the alicyclic organic group may partially or entirely be replaced with fluorine or hydroxyl group, and two hydrogen atoms on the same carbon constituting the alicyclic organic group may be replaced with a single oxygen atom to make a keto group,
a $C_{6-20}$ aryl group, a $C_{1-10}$ straight-chain or branched alkoxyl group, wherein hydrogen atoms of the alkoxyl group may partially or entirely be replaced with fluorine or hydroxyl group,
a $C_{6-20}$ aryloxy group, wherein hydrogen atoms of the aryloxy group may partially or entirely be replaced with fluorine or hydroxyl group,
a $C_{2-10}$ straight-chain or branched alkylcarbonyl group, wherein hydrogen atoms of the alkylcarbonyl group may partially or entirely be replaced with fluorine or hydroxyl group,
a $C_{7-20}$ arylcarbonyl group, wherein hydrogen atoms of the arylcarbonyl group may partially or entirely be replaced with fluorine or hydroxyl group,
a $C_{2-10}$ straight-chain or branched alkylcarbonyloxy group, wherein hydrogen atoms of the alkylcarbonyloxy group may partially or entirely be replaced with fluorine or hydroxyl group,
a $C_{7-20}$ arylcarbonyloxy group, wherein hydrogen atoms of the arylcarbonyloxy group may partially or entirely be replaced with fluorine or hydroxyl group, a C$_{1-10}$ straight-chain or branched alkoxycarbonyl group, wherein hydrogen atoms of the alkoxycarbonyl group may partially or entirely be replaced with fluorine or hydroxyl group, or a C$_{7-20}$ aryloxycarbonyl group, wherein hydrogen atoms of the aryloxycarbonyl group may partially or entirely be replaced with fluorine or hydroxyl group b, wherein n represents 0 or 1, wherein, in case that n is 0, p represents a substituted or unsubstituted C$_{1-20}$ alkyl group, or substituted or unsubstituted C$_{6-15}$ aryl group, wherein in case that n is 1, p represents a single bond, substituted or unsubstituted C$_{1-20}$ alkylene group, or substituted or unsubstituted C$_{6-15}$ arylene group, wherein A represents a cyano group, trifluoromethyl group, perfluoroethyl group, perfluoropropyl group, 5H-perfluoropentyl group, 6H-perfluorohexyl group, nitro group or methyl group, and wherein in case that n is 1, both of A may be attached to each other, thereby forming a C$_6$ ring together with carbon atoms to which they are attached.

4. A photoacid generator containing a fluorine-containing oximesulfonate compound according to claim 3.

5. Triphenylsulfonium 2-(1'-adamantane)carbonyloxy-1,1-difluoroethanesulfonate.

6. Triphenylsulfonium 2-(3'-hydroxy-1'-adamantane)carbonyloxy-1,1-difluoroethanesulfonate.

7. A resist composition comprising a base resin, an acid generator and a solvent, wherein:

the acid generator is an acid generator that generates fluorine-containing sulfonic acid represented by the following formula (4)

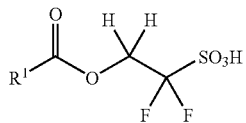

(4)

wherein R$^1$ represents a C$_{1-10}$ straight-chain or branched alkyl group, wherein hydrogen atoms of the alkyl group may partially or entirely be replaced with fluorine or hydroxyl group, and two hydrogen atoms on the same carbon constituting the alkyl group may be replaced with a single oxygen atom to make a keto group, a C$_{1-10}$ straight-chain or branched alkenyl group having a double bond at an end portion at least, wherein hydrogen atoms of the end alkenyl group may partially or entirely be replaced with fluorine or hydroxyl group, and two hydrogen atoms on the same carbon constituting the end alkenyl group may be replaced with a single oxygen atom to make a keto group, a C$_{3-20}$ alicyclic organic group, wherein hydrogen atoms of the alicyclic organic group may partially or entirely be replaced with fluorine or hydroxyl group, and two hydrogen atoms on the same carbon constituting the alicyclic organic group may be replaced with a single oxygen atom to make a keto group, a C$_{6-20}$ aryl group, a C$_{1-10}$ straight-chain or branched alkoxyl group, wherein hydrogen atoms of the alkoxyl group may partially or entirely be replaced with fluorine or hydroxyl group, a C$_{6-20}$ aryloxy group, wherein hydrogen atoms of the aryloxy group may partially or entirely be replaced with fluorine or hydroxyl group, a C$_{2-10}$ straight-chain or branched alkylcarbonyl group, wherein hydrogen atoms of the alkylcarbonyl group may partially or entirely be replaced with fluorine or hydroxyl group, a C$_{7-20}$ arylcarbonyl group, wherein hydrogen atoms of the arylcarbonyl group may partially or entirely be replaced with fluorine or hydroxyl group, a C$_{2-10}$ straight-chain or branched alkylcarbonyloxy group, wherein hydrogen atoms of the alkylcarbonyloxy group may partially or entirely be replaced with fluorine or hydroxyl group, a C$_{7-20}$ arylcarbonyloxy group, wherein hydrogen atoms of the arylcarbonyloxy group may partially or entirely be replaced with fluorine or hydroxyl group, a C$_{1-10}$ straight-chain or branched alkoxycarbonyl group, wherein hydrogen atoms of the alkoxycarbonyl group may partially or entirely be replaced with fluorine or hydroxyl group, or a C$_{7-20}$ aryloxycarbonyl group wherein hydrogen atoms of the aryloxycarbonyl group may partially or entirely be replaced with fluorine or hydroxyl group, and the acid generator that generates fluorine-containing sulfonic acid represented by the above formula (4) is a fluorine-containing N-sulfonyloxyimide compound represented by the following formula (6),

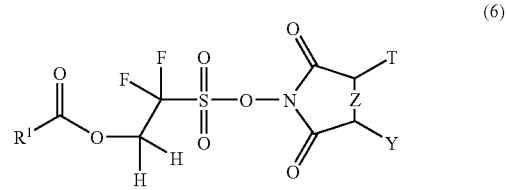

(6)

wherein R$^1$ has the same meaning as that of R$^1$ in formula (4), wherein Z represents a single bond, double bond, methylene group or oxygen atom, and wherein T and Y independently represent hydrogen atoms or C$_{1-10}$ substituted or unsubstituted alkyl groups, or T and Y jointly may form an alicyclic structure, aromatic ring structure or hetero ring structure by including carbon atoms to which they are attached.

8. A resist composition comprising a base resin, an acid generator and a solvent, wherein:

the acid generator is an acid generator that generates fluorine-containing sulfonic acid represented by the following formula (4)

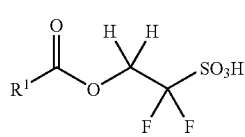

(4)

wherein R$^1$ represents a C$_{1-10}$ straight-chain or branched alkyl group, wherein hydrogen atoms of the alkyl group may partially or entirely be replaced with fluorine or hydroxyl group, and two hydrogen atoms on the same carbon constituting the alkyl group may be replaced with a single oxygen atom to make a keto group, a $C_{1-10}$ straight-chain or branched alkenyl group having a double bond at an end portion at least, wherein hydrogen atoms of the end alkenyl group may partially or entirely be replaced with fluorine or hydroxyl group, and two hydrogen atoms on the same carbon constituting the end alkenyl group may be replaced with a single oxygen atom to make a keto group, a $C_{3-20}$ alicyclic organic group, wherein hydrogen atoms of the alicyclic organic group may partially or entirely be replaced with fluorine or hydroxyl group, and two hydrogen atoms on the same carbon constituting the alicyclic organic group may be replaced with a single oxygen atom to make a keto group, a $C_{6-20}$ aryl group, a $C_{1-10}$ straight-chain or branched alkoxyl group, wherein hydrogen atoms of the alkoxyl group may partially or entirely be replaced with fluorine or hydroxyl group, a $C_{6-20}$ aryloxy group, wherein hydrogen atoms of the aryloxy group may partially or entirely be replaced with fluorine or hydroxyl group, a $C_{2-10}$ straight-chain or branched alkylcarbonyl group, wherein hydrogen atoms of the alkylcarbonyl group may partially or entirely be replaced with fluorine or hydroxyl group, a $C_{7-20}$ arylcarbonyl group, wherein hydrogen atoms of the arylcarbonyl group may partially or entirely be replaced with fluorine or hydroxyl group, a $C_{2-10}$ straight-chain or branched alkylcarbonyloxy group, wherein hydrogen atoms of the alkylcarbonyloxy group may partially or entirely be replaced with fluorine or hydroxyl group, a $C_{7-20}$ arylcarbonyloxy group, wherein hydrogen atoms of the arylcarbonyloxy group may partially or entirely be replaced with fluorine or hydroxyl group, a $C_{1-10}$ straight-chain or branched alkoxycarbonyl group, wherein hydrogen atoms of the alkoxycarbonyl group may partially or entirely be replaced with fluorine or hydroxyl group, or a $C_{7-20}$ aryloxycarbonyl group wherein hydrogen atoms of the aryloxycarbonyl group may partially or entirely be replaced with fluorine or hydroxyl group, and the acid generator that generates fluorine-containing sulfonic acid represented by the above formula (4) is a fluorine-containing oximesulfonate compound represented by the following formula (7),

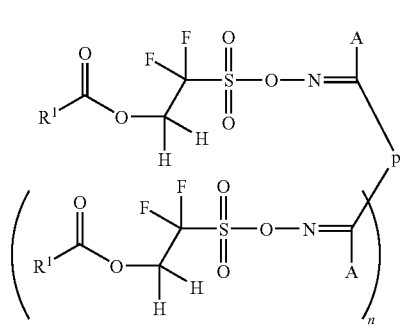

(7)

wherein $R^1$ has the same meaning as that of $R^1$ in formula (4), wherein n represents 0 or 1, wherein, in case that n is 0, p represents a substituted or unsubstituted $C_{1-20}$ alkyl group, or substituted or unsubstituted $C_{6-15}$ aryl group, wherein in case that n is 1, p represents a single bond, substituted or unsubstituted $C_{1-20}$ alkylene group, or substituted or unsubstituted $C_{6-15}$ arylene group, wherein A represents a cyano group, trifluoromethyl group, perfluoroethyl group, perfluoropropyl group, 5H-perfluoropentyl group, 6H-perfluorohexyl group, nitro group or methyl group, wherein in case that n is 1, both of A may be attached to each other, thereby forming a $C_6$ ring together with carbon atoms to which they are attached.

9. A resist composition comprising a base resin, an acid generator and a solvent, wherein:

the acid generator is an acid generator that generates fluorine-containing sulfonic acid represented by the following formula (4)

$$\underset{R^1}{\phantom{X}}\overset{O}{\underset{\phantom{X}}{\|}}\phantom{X}O\phantom{X}\overset{H\phantom{X}H}{\underset{F\phantom{X}F}{|\phantom{X}|}}\phantom{X}SO_3H \quad (4)$$

wherein $R^1$ represents a $C_{1-10}$ straight-chain or branched alkyl group, wherein hydrogen atoms of the alkyl group may partially or entirely be replaced with fluorine or hydroxyl group, and two hydrogen atoms on the same carbon constituting the alkyl group may be replaced with a single oxygen atom to make a keto group, a $C_{1-10}$ straight-chain or branched alkenyl group having a double bond at an end portion at least, wherein hydrogen atoms of the end alkenyl group may partially or entirely be replaced with fluorine or hydroxyl group, and two hydrogen atoms on the same carbon constituting the end alkenyl group may be replaced with a single oxygen atom to make a keto group, a $C_{3-20}$ alicyclic organic group, wherein hydrogen atoms of the alicyclic organic group may partially or entirely be replaced with fluorine or hydroxyl group, and two hydrogen atoms on the same carbon constituting the alicyclic organic group may be replaced with a single oxygen atom to make a keto group, a $C_{6-20}$ aryl group, a $C_{1-10}$ or branched alkoxyl group, wherein hydrogen atoms of the alkoxyl group may partially or entirely be replaced with fluorine or hydroxyl group, a $C_{6-20}$ aryloxy group, wherein hydrogen atoms of the aryloxy group may partially or entirely be replaced with fluorine or hydroxyl group, a $C_{2-10}$ straight-chain or branched alkylcarbonyl group, wherein hydrogen atoms of the alkylcarbonyl group may partially or entirely be replaced with fluorine or hydroxyl group, a $C_{7-20}$ arylcarbonyl group, wherein hydrogen atoms of the arylcarbonyl group may partially or entirely be replaced with fluorine or hydroxyl group, a $C_{2-10}$ straight-chain or branched alkylcarbonyloxy group, wherein hydrogen atoms of the alkylcarbonyloxy group may partially or entirely be replaced with fluorine or hydroxyl group, a C$_{7-20}$ arylcarbonyloxy group, wherein hydrogen atoms of the arylcarbonyloxy group may partially or entirely be replaced with fluorine or hydroxyl group, a C$_{1-10}$ straight-chain or branched alkoxycarbonyl group, wherein hydrogen atoms of the alkoxycarbonyl group may partially or entirely be replaced with fluorine or hydroxyl group, or a C$_{7-20}$ aryloxycarbonyl group wherein hydrogen atoms of the aryloxycarbonyl group may partially or entirely be replaced with fluorine or hydroxyl group, and the base resin is a polymer compound containing a repeating unit represented by the following formula (10)

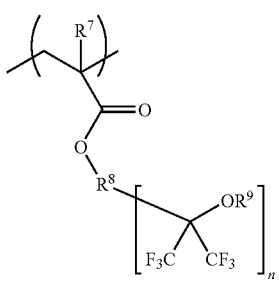

(10)

wherein R$^7$ represents a hydrogen atom, halogen atom, hydrocarbon group, or fluorine-containing alkyl group, wherein R$^8$ is an alkyl group that is straight-chain or optionally branched, an alkyl group having a ring structure, an aromatic ring, or a complex substituent of them, and a part of that may be fluorinated, wherein R$^9$ is a hydrogen atom, and a hydrocarbon group optionally branched, a fluorine-containing alkyl group, or a ring form having an aromatic or aliphatic ring, and may contain bond such as oxygen or carbonyl, wherein n represents an integer of 1-2.

10. A resist composition according to claim 9, characterized in that in claim 9 the repeating unit is a repeating unit represented by the following formula (11)

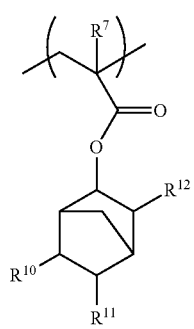

(11)

wherein R$^7$ is defined as in formula (10), wherein any one of R$^{10}$, R$^{11}$ and R$^{12}$ is CF$_3$C(CF$_3$)(OH)CH$_2$— group, and the remaining two are hydrogen.

11. A resist composition according to claim 9, characterized in that in claim 9 the repeating unit is a repeating unit represented by the following formula (12)

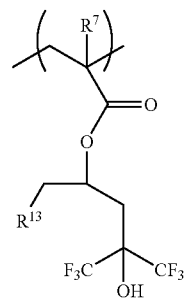

(12)

wherein R$^7$ has the same meaning as that of R$^7$ in formula (10), wherein R$^{13}$ is a hydrogen atom, methyl group, ethyl group, n-propyl group, isopropyl group, n-butyl group, sec-butyl group, tert-butyl group, fluoromethyl group, difluoromethyl group, trifluoromethyl group, or perfluoroethyl group.

12. A resist composition comprising a base resin, an acid generator and a solvent, wherein:

the acid generator is an acid generator that generates fluorine-containing sulfonic acid represented by the following formula (4)

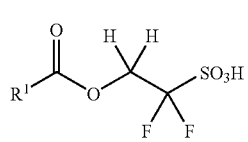

(4)

wherein R$^1$ represents a C$_{1-10}$ straight-chain or branched alkyl group, wherein hydrogen atoms of the alkyl group may partially or entirely be replaced with fluorine or hydroxyl group, and two hydrogen atoms on the same carbon constituting the alkyl group may be replaced with a single oxygen atom to make a keto group, a C$_{1-10}$ straight-chain or branched alkenyl group having a double bond at an end portion at least, wherein hydrogen atoms of the end alkenyl group may partially or entirely be replaced with fluorine or hydroxyl group, and two hydrogen atoms on the same carbon constituting the end alkenyl group may be replaced with a single oxygen atom to make a keto group, a C$_{3-20}$ alicyclic organic group, wherein hydrogen atoms of the alicyclic organic group may partially or entirely be replaced with fluorine or hydroxyl group, and two hydrogen atoms on the same carbon constituting the alicyclic organic group may be replaced with a single oxygen atom to make a keto group, a C$_{6-20}$ aryl group, a C$_{1-10}$ straight-chain or branched alkoxyl group, wherein hydrogen atoms of the alkoxyl group may partially or entirely be replaced with fluorine or hydroxyl group, a C$_{6-20}$ aryloxy group, wherein hydrogen atoms of the aryloxy group may partially or entirely be replaced with fluorine or hydroxyl group, a C$_{2-10}$ straight-chain or branched alkylcarbonyl group, wherein hydrogen atoms of the alkylcarbonyl group may partially or entirely be replaced with fluorine or hydroxyl group, a $C_{7-20}$ arylcarbonyl group, wherein hydrogen atoms of the arylcarbonyl group may partially or entirely be replaced with fluorine or hydroxyl group, a $C_{2-10}$ straight-chain or branched alkylcarbonyloxy group, wherein hydrogen atoms of the alkylcarbonyloxy group may partially or entirely be replaced with fluorine or hydroxyl group, a $C_{7-20}$ arylcarbonyloxy group, wherein hydrogen atoms of the arylcarbonyloxy group may partially or entirely be replaced with fluorine or hydroxyl group, a $C_{1-10}$ straight-chain or branched alkoxycarbonyl group, wherein hydrogen atoms of the alkoxycarbonyl group may partially or entirely be replaced with fluorine or hydroxyl group, or a $C_{7-20}$ aryloxycarbonyl group wherein hydrogen atoms of the aryloxycarbonyl group may partially or entirely be replaced with fluorine or hydroxyl group, and the base resin is a polymer compound containing a repeating unit represented by the following formula (8)

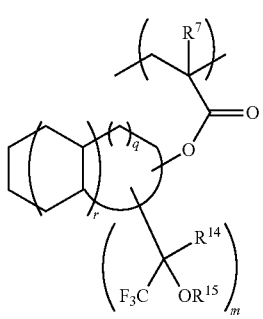

(8)

wherein $R^7$ represents a hydrogen atom, halogen atom, hydrocarbon group, or fluorine-containing alkyl group, wherein $R^{14}$ represents a methyl group or trifluoromethyl group, wherein $R^{15}$ is a hydrogen atom, a $C_{1-25}$ straight-chain, branched or cyclic hydrocarbon group or a group containing an aromatic hydrocarbon group, and a part of that may contain fluorine atom, oxygen atom or carbonyl bond, wherein r represents an arbitrary integer of 0-2, wherein m and q represent arbitrary integers of 1-8, and satisfy m≦q+2, and wherein, in case that $R^{14}$-$R^{15}$ are in plural number, $R^{14}$-$R^{15}$ may respectively be the same or different.

13. A resist composition comprising a base resin, an acid generator and a solvent, wherein:

the acid generator is an acid generator that generates fluorine-containing sulfonic acid represented by the following formula (4)

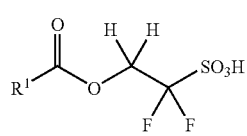

(4)

wherein $R^1$ represents a $C_{1-10}$ straight-chain or branched alkyl group, wherein hydrogen atoms of the alkyl group may partially or entirely be replaced with fluorine or hydroxyl group, and two hydrogen atoms on the same carbon constituting the alkyl group may be replaced with a single oxygen atom to make a keto group, a $C_{1-10}$ straight-chain or branched alkenyl group having a double bond at an end portion at least, wherein hydrogen atoms of the end alkenyl group may partially or entirely be replaced with fluorine or hydroxyl group, and two hydrogen atoms on the same carbon constituting the end alkenyl group may be replaced with a single oxygen atom to make a keto group, a $C_{3-20}$ alicyclic organic group, wherein hydrogen atoms of the alicyclic organic group may partially or entirely be replaced with fluorine or hydroxyl group, and two hydrogen atoms on the same carbon constituting the alicyclic organic group may be replaced with a single oxygen atom to make a keto group, a $C_{6-20}$ aryl group, a $C_{1-10}$ straight-chain or branched alkoxyl group, wherein hydrogen atoms of the alkoxyl group may partially or entirely be replaced with fluorine or hydroxyl group, a $C_{6-20}$ aryloxy group, wherein hydrogen atoms of the aryloxy group may partially or entirely be replaced with fluorine or hydroxyl group, a $C_{2-10}$ straight-chain or branched alkylcarbonyl group, wherein hydrogen atoms of the alkylcarbonyl group may partially or entirely be replaced with fluorine or hydroxyl group, a $C_{7-20}$ arylcarbonyl group, wherein hydrogen atoms of the arylcarbonyl group may partially or entirely be replaced with fluorine or hydroxyl group, a $C_{2-10}$ straight-chain or branched alkylcarbonyloxy group, wherein hydrogen atoms of the alkylcarbonyloxy group may partially or entirely be replaced with fluorine or hydroxyl group, a $C_{7-20}$ arylcarbonyloxy group, wherein hydrogen atoms of the arylcarbonyloxy group may partially or entirely be replaced with fluorine or hydroxyl group, a $C_{1-10}$ straight-chain or branched alkoxycarbonyl group, wherein hydrogen atoms of the alkoxycarbonyl group may partially or entirely be replaced with fluorine or hydroxyl group, or a $C_{7-20}$ aryloxycarbonyl group wherein hydrogen atoms of the aryloxycarbonyl group may partially or entirely be replaced with fluorine or hydroxyl group, and the base resin contains a repeating unit represented by the following formula (9)

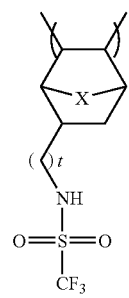

(9)

wherein X represents any of —$CH_2$—, —O—, and —S—, and t represents an integer of 1-6.

14. A photoacid generator containing triphenylsulfonium 2-(1'-adamantane)carbonyloxy-1,1-difluoroethanesulfonate.

15. A photoacid generator containing triphenylsulfonium 2-(3'-hydroxy-1'-adamantane)carbonyloxy-1,1-difluoroethanesulfonate.

16. A resist composition comprising a base resin, an acid generator and a solvent, wherein
the acid generator is an acid generator that generates a fluorine-containing sulfonic acid represented by the following formula (4)

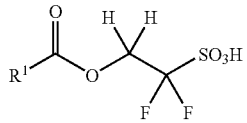
(4)

wherein $R^1$ represents:
a $C_{1-10}$ straight-chain or branched alkyl group, wherein hydrogen atoms of the alkyl group may partially or entirely be replaced with fluorine or hydroxyl group, and two hydrogen atoms on the same carbon constituting the alkyl group may be replaced with a single oxygen atom to make a keto group,
a $C_{1-10}$ straight-chain or branched alkenyl group having a double bond at an end portion at least, wherein hydrogen atoms of the end alkenyl group may partially or entirely be replaced with fluorine or hydroxyl group, and two hydrogen atoms on the same carbon constituting the end alkenyl group may be replaced with a single oxygen atom to make a keto group,
a $C_{3-20}$ alicyclic organic group, wherein hydrogen atoms of the alicyclic organic group may partially or entirely be replaced with fluorine or hydroxyl group, and two hydrogen atoms on the same carbon constituting the alicyclic organic group may be replaced with a single oxygen atom to make a keto group,
a $C_{6-20}$ aryl group, a $C_{1-10}$ straight-chain or branched alkoxyl group, wherein hydrogen atoms of the alkoxyl group may partially or entirely be replaced with fluorine or hydroxyl group,
a $C_{6-20}$ aryloxy group, wherein hydrogen atoms of the aryloxy group may partially or entirely be replaced with fluorine or hydroxyl group,
a $C_{2-10}$ straight-chain or branched alkylcarbonyl group, wherein hydrogen atoms of the alkylcarbonyl group may partially or entirely be replaced with fluorine or hydroxyl group,
a $C_{7-20}$ arylcarbonyl group, wherein hydrogen atoms of the arylcarbonyl group may partially or entirely be replaced with fluorine or hydroxyl group,
a $C_{2-10}$ straight-chain or branched alkylcarbonyloxy group, wherein hydrogen atoms of the alkylcarbonyloxy group may partially or entirely be replaced with fluorine or hydroxyl group,
a $C_{7-20}$ arylcarbonyloxy group, wherein hydrogen atoms of the arylcarbonyloxy group may partially or entirely be replaced with fluorine or hydroxyl group,
a $C_{1-10}$ straight-chain or branched alkoxycarbonyl group, wherein hydrogen atoms of the alkoxycarbonyl group may partially or entirely be replaced with fluorine or hydroxyl group, or a $C_{7-20}$ aryloxycarbonyl group wherein hydrogen atoms of the aryloxycarbonyl group may partially or entirely be replaced with fluorine or hydroxyl group,
and
the acid generator that generates the fluorine-containing sulfonic acid represented by formula (4) is triphenylsulfonium 2-(1'-adamantane)-carbonyloxy-1,1-difluoroethanesulfonate.

17. A resist composition comprising a base resin, an acid generator and a solvent, wherein
the acid generator is an acid generator that generates a fluorine-containing sulfonic acid represented by the following formula (4)

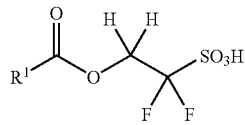
(4)

wherein $R^1$ represents:
a $C_{1-10}$ straight-chain or branched alkyl group, wherein hydrogen atoms of the alkyl group may partially or entirely be replaced with fluorine or hydroxyl group, and two hydrogen atoms on the same carbon constituting the alkyl group may be replaced with a single oxygen atom to make a keto group,
a $C_{1-10}$ straight-chain or branched alkenyl group having a double bond at an end portion at least, wherein hydrogen atoms of the end alkenyl group may partially or entirely be replaced with fluorine or hydroxyl group, and two hydrogen atoms on the same carbon constituting the end alkenyl group may be replaced with a single oxygen atom to make a keto group,
a $C_{3-20}$ alicyclic organic group, wherein hydrogen atoms of the alicyclic organic group may partially or entirely be replaced with fluorine or hydroxyl group, and two hydrogen atoms on the same carbon constituting the alicyclic organic group may be replaced with a single oxygen atom to make a keto group,
a $C_{6-20}$ aryl group, a $C_{1-10}$ straight-chain or branched alkoxyl group, wherein hydrogen atoms of the alkoxyl group may partially or entirely be replaced with fluorine or hydroxyl group,
a $C_{6-20}$ aryloxy group, wherein hydrogen atoms of the aryloxy group may partially or entirely be replaced with fluorine or hydroxyl group,
a $C_{2-10}$ straight-chain or branched alkylcarbonyl group, wherein hydrogen atoms of the alkylcarbonyl group may partially or entirely be replaced with fluorine or hydroxyl group,
a $C_{7-20}$ arylcarbonyl group, wherein hydrogen atoms of the arylcarbonyl group may partially or entirely be replaced with fluorine or hydroxyl group,
a $C_{2-10}$ straight-chain or branched alkylcarbonyloxy group, wherein hydrogen atoms of the alkylcarbonyloxy group may partially or entirely be replaced with fluorine or hydroxyl group,
a $C_{7-20}$ arylcarbonyloxy group, wherein hydrogen atoms of the arylcarbonyloxy group may partially or entirely be replaced with fluorine or hydroxyl group,
a $C_{1-10}$ straight-chain or branched alkoxycarbonyl group, wherein hydrogen atoms of the alkoxycarbonyl group may partially or entirely be replaced with fluorine or hydroxyl group, or a $C_{7-20}$ aryloxycarbonyl group wherein hydrogen atoms of the aryloxycarbonyl group may partially or entirely be replaced with fluorine or hydroxyl group,
and
the acid generator that generates the fluorine-containing sulfonic acid represented by formula (4) is triphenylsulfonium 2-(3'-hydroxy-1'-adamantane)-carbonyloxy-1,1-difluoroethanesulfonate.

* * * * *